US011299753B2

(12) United States Patent
Mahoney et al.

(10) Patent No.: US 11,299,753 B2
(45) Date of Patent: *Apr. 12, 2022

(54) METHOD FOR COUNTERSELECTION IN MICROORGANISMS

(71) Applicant: Zymergen Inc., Emeryville, CA (US)

(72) Inventors: Tara F. Mahoney, San Francisco, CA (US); Amanda Renae Reider Apel, Alameda, CA (US); Paloma Rueda Romero, Berkeley, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/397,540

(22) Filed: Aug. 9, 2021

(65) Prior Publication Data

US 2021/0371882 A1    Dec. 2, 2021

Related U.S. Application Data

(63) Continuation of application No. 17/029,200, filed on Sep. 23, 2020, now Pat. No. 11,111,507.

(60) Provisional application No. 62/904,285, filed on Sep. 23, 2019.

(51) Int. Cl.
| | | |
|---|---|---|
| *C12N 15/90* | (2006.01) | |
| *C12N 1/20* | (2006.01) | |
| *C12N 9/00* | (2006.01) | |

(52) U.S. Cl.
CPC ............. *C12N 15/90* (2013.01); *C12N 1/20* (2013.01); *C12N 9/93* (2013.01); *C12Y 601/0102* (2013.01); *C12N 2501/999* (2013.01)

(58) Field of Classification Search
CPC .......................... C12N 15/90; C12Y 601/0102
See application file for complete search history.

(56) References Cited

U.S. PATENT DOCUMENTS

| | | | |
|---|---|---|---|
| 6,090,592 | A | 7/2000 | Adams et al. |
| 6,300,070 | B1 | 10/2001 | Boles et al. |
| 7,115,400 | B1 | 10/2006 | Adessi et al. |
| 11,111,507 | B2 | 9/2021 | Mahoney et al. |
| 2007/0292918 | A1 | 12/2007 | Stelman et al. |
| 2010/0137143 | A1 | 6/2010 | Rothberg et al. |
| 2010/0304982 | A1 | 12/2010 | Hinz et al. |
| 2015/0211022 | A1 | 7/2015 | Walker et al. |
| 2021/0087586 | A1 | 3/2021 | Mahoney et al. |

FOREIGN PATENT DOCUMENTS

| | | |
|---|---|---|
| EP | 0972081 B1 | 6/2007 |
| WO | WO 2011/154147 A1 | 12/2011 |
| WO | WO 2015/116734 A1 | 8/2015 |
| WO | WO 2017/100377 A1 | 6/2017 |
| WO | WO 2021/061694 A1 | 4/2021 |

OTHER PUBLICATIONS

Aslanidis and De Jong, "Ligation-independent cloning of PCR products (LIC-PCR)." Nucleic Acids Research (Oct. 25, 1990; 18(20): 6069-6074.
Becker and Guarente, "High-efficiency transformation of yeast by electroporation." Methods in Enzymology (1991); 194: 182-187.
Bentley, et al., "Accurate whole human genome sequencing using reversible terminator chemistry." Nature (2008); 456(7218): 53-59.
Christie and Gordon, "The Agrobacterium Ti plasmids." Microbiology Spectrum (2014); 2(6): pp. 1-18.
Dong and Zhang, "Current development in genetic engineering strategies of *Bacillus* species". Microb Cell Fact (2014); 13.1: 1-11.
Drmanac, et al., "Human genome sequencing using unchained base reads on self-assembling DNA nanoarrays." Science (Jan. 1, 2010); 327(5961): 78-81.
Engler, et al., "A One Pot, One Step, Precision Cloning Method with High Throughput Capability." PLoS One (Nov. 2008); 3.11: e3647, pp. 1-7. Epub Nov. 5, 2008.
Fox, et al. "Improving catalytic function by ProSAR-driven enzyme evolution." Nature Biotechnology (Feb. 18, 2007); 25(3): 338-344.
GenBank Accession No. AJ841297.1 Bacillus amyloliquefaciens pheS gene for phenylalanyl-tRNA synthetase alpha chain, strain FZB42. Sep. 22, 2004 [online]. [Retrieved on Jan. 19, 2021]. Retrieved from the internet: <URL:https://www.ncbi.nlm.nih.gov/nucleotide/AJ841297.1?report=GenBank&log$=nuclalign&blast_rank=78&RID=0E8P7M2D016>, Retrieved on Jan. 1, 2019, 2 pages.
Gibson, et al., "Enzymatic assembly of DNA molecules up to several hundred kilobases." Nature Methods (Apr. 12, 2009); 6(5): 343-345.
Guan, et al., "Construction of a highly active secretory expression system via an engineered dual promoter and a highly efficient signal peptide in Bacillus subtilis." N Biotechnol. (May 25, 2016); 33(3): 372-379. Epub Jan. 25, 2016.
Guiziou, et al., "A part toolbox to tune genetic expression in Bacillus subtilis." Nucleic Acids Res. (Sep. 6, 2016); 44(15): 7495-7508. Epub Jul. 8, 2016.
International Patent Application No. PCT/US2020/052093, Invitation to Pay Additional Fees mailed Dec. 8, 2020, 4 pages.
International Patent Application No. PCT/US2020/052093, International Search Report and Written Opinion dated Feb. 9, 2021, 23 pages.
Kast and Hennecke, "Amino acid substrate specificity of *Escherichia coli* phenylalanyl-tRNA synthetase altered by distinct mutations." J Mol Biol. (Nov. 5, 1991); 222(1): 99-124.
Khanna, et al. "Identification of the template binding polypeptide in the pea chloroplast transcriptional complex." Nucleic Acids Research (1992); 20(1): 69-74.
Kharchenko, et al., "Improving the selection efficiency of the counter-selection marker pheS for the genetic engineering of Bacillus amyloliquefaciens." J Microbiol Methods. (May 2018); 148: 18-21. Epub Mar. 27, 2018.

(Continued)

*Primary Examiner* — Antonio Galisteo Gonzalez
(74) *Attorney, Agent, or Firm* — Cooley LLP

(57) ABSTRACT

The present disclosure is directed to methods of scarless genomic engineering in microorganisms, such as *Bacillus*, and provides for new molecular tools and methods which enable scarless genetic editing using at least one counterselectable marker that has been codon optimized for the microorganism. The disclosure allows for the high-throughput introduction of stable genetic edits to a genome using either plasmid or linear DNA constructs for genetic engineering.

30 Claims, 9 Drawing Sheets

Specification includes a Sequence Listing.

(56) References Cited

OTHER PUBLICATIONS

Koren, et al., "Influence of homology size and polymorphism on plasmid integration in the yeast CYC1 DNA region". Current Genetics (May 2000); 37: 292-297.
Kotera and Nagai, "A high-throughput and single-tube recombination of crude PCR products using a DNA polymerase inhibitor and type IIS restriction enzyme." Journal of Biotechnology (Oct. 10, 2008); 137.1: 1-7. Epub Jul. 23, 2008.
Liu, et al., "Construction, Model-Based Analysis, and Characterization of a Promoter Library for Fine-Tuned Gene Expression in Bacillus subtilis." ACS Synth. Biol. (Jun. 26, 2018); 7(7): 1785-1797.
Maguin, et al., "New Thermosensitive Plasmid for Gram-Positive Bacteria." J Bacteriol. (Sep. 1992); 174(17): 5633-5638.
Margulies, et al., "Genome sequencing in microfabricated high-density picolitre reactors." Nature (Sep. 15, 2005); 437(7057): 376-380. Epub Jul. 31, 2005.
Meng, et al., "Enhanced Expression of Pullulanase in Bacillus subtilis by New Strong Promoters Mined From Transcriptome Data, Both Alone and in Combination". Front Microbiol. (2018); 9: 2635. Epub Nov. 2, 2018.
Miyazaki, K., "Molecular engineering of a PheS counterselection marker for improved operating efficiency in *Escherichia coli*". BioTechniques (Feb. 1, 2015); 58(2): 86-88. eCollection Feb. 2015.
Murray, et al., "Codon usage in plant genes." Nucleic Acids Research (Jan. 25, 1989); 17(2): 477-498.
Nakashima and Miyazaki, "Bacterial cellular engineering by genome editing and gene silencing." International Journal of Molecular Sciences (Feb. 18, 2014); 15(2): 2773-2793.
Reyrat, et al., "Counterselectable markers: untapped tools for bacterial genetics and pathogenesis." Infection and Immunity (Sep. 1998); 66(9): 4011-4017.
Salis, et al., "Automated Design of Synthetic Ribosome Binding Sites to Precisely Control Protein Expression." Nat Biotechnol. (Oct. 2009); 27(10): 946-950. Epub Oct. 4, 2009.
Schuster, et al., "Use of the counter selectable marker PheS for genome engineering in *Staphylococcus aureus*". Microbiology (May 2019); 165(5): 572-584. Epub Apr. 3, 2019.
Shatalin and Neyfakh, "Efficient gene inactivation in Bacillus anthracis." FEMS Microbiol Lett. (Apr. 15, 2005); 245(2): 315-319.
Song, et al., "Promoter Screening from Bacillus subtilis in Various Conditions Hunting for Synthetic Biology and Industrial Applications." PLoS One. (2016); 11(7): e0158447. Epub Jul. 5, 2016.
Su, et al., "*Escherichia coli* mutS-encoded protein binds to mismatched DNA base pairs." Proc. Natl. Acad. Sci. U. S. A. (Jul. 15, 1986); 83(14): 5057-5061.
Tear, et al., "Excision of Unstable Artificial Gene-Specific Inverted Repeats Mediates Scar-Free Gene Deletions in *Escherichia coli*." Applied Biochemistry and Biotechnology (Feb. 2015); 175(4): 1858-1867. Epub Nov. 27, 2014.
Trauth and Bischofs, "Ectopic Integration Vectors for Generating Fluorescent Promoter Fusions in Bacillus subtilis with Minimal Dark Noise", PLoS One (May 29, 2014); 9(5): e98360, 9 pages.
Vagner, et al., "A vector for systematic gene inactivation in Bacillus subtilis". Microbiology (Reading). (Nov. 1998); 144 ( Pt 11): 3097-3104.
Wagner, et al., "Mutation detection using immobilized mismatch binding protein (MutS)." Nucleic Acids Research (Oct. 11, 1995); 23(19): 3944-3948.
Wang and Sun, "Phylogenetic relationships between *Bacillus* species and related genera inferred from 16s rDNA sequences". Braz J Microbiol. (Jul.-Sep. 2009); 40(3): 505-521. Epub Sep. 1, 2009.
Weber, et al., "Assembly of designer TAL effectors by Golden Gate cloning." PLoS One (2011); 6.5: e19722, pp. 1-5. Epub May 19, 2011.
Wu, et al., "Engineering a Bacillus subtilis expression-secretion system with a strain deficient in six extracellular proteases." J Bacteriol. (Aug. 1991); 173(16): 4952-4958.
Yang, et al., "Generation of an Artificial Double Promoter for Protein Expression in Bacillus subtilis through a Promoter Trap System". PLoS One. (2013); 8(2): e56321. Epub Feb. 8, 2013.
Zahir, et al., "High-throughput time-resolved morphology screening in bacteria reveals phenotypic responses to antibiotics." Communications Biology (2019); 2: 269.
Zhang, et al., "High-level extracellular protein production in Bacillus subtilis using an optimized dual-promoter expression system". Microb Cell Fact. (Feb. 20, 2017); 16(1): 32, 15 pages.
Zhou, et al., "pheS, an effective host-genotype-independent counter-selectable marker for marker-free chromosome deletion in Bacillus amyloliquefaciens." Appl Microbiol Biotechnol. (Jan. 2017); 101(1): 217-227. Epub Oct. 11, 2016.

Non-functional PheS
LB+ 4-CP 10mM

**PliaG-PheS(\*\*CO)-TgyrA**
LB+ 4-CP 10mM

Fig. 5

```
SEQ ID NO: 1     1 ATGGAAGAGAAGCTTAAACAGCTCGAACTGGAAGCTGCAGAAAAGTAGA   50
                   ||||||||||||.||.||||||||.||.|||||||||.||.||.||||||||
SEQ ID NO: 2     1 ATGGAAGAGAAACTCAAACAGCTTGAGCTGGAAGCAGCCGAGAAAGTAGA   50

SEQ ID NO: 1    51 AGCGGCTGGT-----TCATTAAAAGAAGTTAACGATATTCGGGTGCAATAT   96
                   .||||||.|||     ||     ||||||.||.||||||.||||||||.|||||.
SEQ ID NO: 2    51 GGCGGCGGGTAGCCTC-----AAAGAGGTGAACGACATTCGGGTACAATAC   96

SEQ ID NO: 1    97 CTCGGAAAAAAGGGCCGATTACAGAAGTTCTCCGCGGCATGGGCAAACT  146
                   ||||||.||.|||||.||.||.||||||||||.|..|.||.|||||.|||||
SEQ ID NO: 2    97 CTCGGTAAGAAAGGCCCAATAACAGAAGTTTTGAGAGGAATGGGGAAACT  146

SEQ ID NO: 1   147 --GTCCGCCGAAGAGCGCCCGAAAATGGGAGCCCTCGCCAATGAAGT----  191
                     ||  ||.||.|||.|.|||||||||||||.||.||||||||||.|||||
SEQ ID NO: 2   147 CAGT---GCTGAGGAGAGACCGAAAATGGGGCGCTCGCCAACGAAGTTCG  194

SEQ ID NO: 1   192 -GAGAGAGCGCATTGCAGCAGCCATAACGGCGAAAAATGAACAGCTTGAA  240
                    ||.|||     ||.||||||||.|||||.|||||||||||||.||||||
SEQ ID NO: 2   195 GGAAAGA----ATCGCAGCAGCTATAACCGCGAAAAATGAACAACTTGAA  240

SEQ ID NO: 1   241 CAAGAAGAGATGAATAAAAAACTCAGCAG------TCAGACGATTGATGTC  295
                   ||||||||.|||||||||.|||.|     |     |||.|||||.||.||.
SEQ ID NO: 2   241 CAAGAAGAAATGAATAAGAAATT------GTCTTCTCAAACGATCGACGTT  285

SEQ ID NO: 1   286 ACATTGCCTGG--CAGTCCGGTAAACATCGGCGGACGCCATCCGCTGACG  333
                   ||..|.||.||   ||  |||||.||.||.|||||...|.|||||||.|||
SEQ ID NO: 2   286 ACTCTCCCAGGATCA--CCGGTCAATATAGGCGGGAGACATCCGCTCACG  333

SEQ ID NO: 1   334 GTCGTTATTGAAGAAATTGAAGATTTATTTATCGGTATGGGATATACCGT  383
                   |||||.||.||.||||.|||||||..|.||||||||.|||||.|||||.||
SEQ ID NO: 2   334 GTCGTGATAGAGGAAATCGAAGACCTCTTTATCGGATGGGTTATACGGT  383

SEQ ID NO: 1   384 AGAAGAAGGCCCTGAAGTGGAAACGGATTATTATAACTTCGAAGCGCTGA  433
                   .||||||||.||||||.||.||||||.||||||||||||||||..|.|
SEQ ID NO: 2   384 GGAAGAAGGACCTGAGGTCGAAACTGATTATTACAATTTCGAGGCTTAA  433

SEQ ID NO: 1   434 ATCTGCCGAAGGAACATCCGGCCCGCGACATGCAGGACAGCTTTTACATT  493
                   |||||||.||.|||||.||.||.||.||.|||||||||||....||||||||.
SEQ ID NO: 2   434 ATCTGCCAAAAGAACACCCTGCGCGGGATATGCAGGATTCTTTTTACATC  483

SEQ ID NO: 1   484 ACAGAAGAAATGCTGATGAGAACGCAGAC--GTCACCGGTGCAGACACGC  531
                   ||.||.||.|||||.|||||||||.|||||| ||  ||.|||||.||.||.
SEQ ID NO: 2   484 ACGGAGGAGATGCTCATGAGAACTCAGACTAGT--CCTGTGCAAACGCGG  531

SEQ ID NO: 1   532 ACGATGGAAAAACATAAAGGAAAAGGCCCCGTCAAAATCATTTGTCCCGG  581
                   |||||||||||.||.|||||||||||||||.||.||.|||||.|||||.||
SEQ ID NO: 2   532 ACGATGGAAAAGCACAAAGGAAAGGGGCCTGTCAAGATCATCTGTCCGGG  581

SEQ ID NO: 1   582 TAAAGTGTATCGCCGTGACAACGATGACGCGACACATTCCCATCAGTTCA  631
                   .||.||.||.|||.|.||.|||||.||||||...|||||.|||
SEQ ID NO: 2   582 GAAGGTCTACCGGCGGGATAACGACGACGCGACTCATAGTCATCAATTCA  631

SEQ ID NO: 1   632 TGCAGATCGAGGGTCTCGTCGTGGACCGCAAAATCAGCATGAGCGACCTG  681
                   |||.||.||||||..||.||.|||||.|||||.||||...|||...||..||
SEQ ID NO: 2   632 TGCAAATTGAGGGCTTGGTAGTGGACCGTAAAATTTCCATGTCTGATTTG  681

SEQ ID NO: 1   682 AAGGCACGCTTGAATTGGTCGCGAAAAAATGTTCGGCCAAGACCGTGA  731
                   ||.||.||.|||||||||.||.||.||.||||||.||.|||||||.|.||
SEQ ID NO: 2   682 AAGGGGACTCTTGAATTAGTTGCTAAGAAAATGTTTGGTCAAGACAGAGA  731
```

Fig. 5 (Continued)

```
SEQ ID NO: 1    732  AATCAGGCTCCGTCCGAGC-TTCTTCCCATTCTCCGAGCCTTCTGTCGAA   780
                     .||..|.||||| ||.|.| ||.||.||.||....||||....||.||.
SEQ ID NO: 2    732  GATACGCCTCCG-CCCATCATTTTTCCGTTTAGTGAGCCAAGCGTAGAG   780

SEQ ID NO: 1    781  GTGGATGTGACCTGCTTTAAGTGCGGCGGACAAGGCTGCTCCGTCTGCAA   830
                     ||.|||||.||.||||||.||.||.|||||.||.||.|||..||||.||
SEQ ID NO: 2    781  GTAGATGTTACGTGCTTCAAATGTGGCGGCCAGGGGTGCAGCGTGTGTAA   830

SEQ ID NO: 1    831  AAAAACAGGCTGGATCGAAATTCTCGGCGCCGGCATGGTTCACCCGAACG   880
                     .||.||.|||||||||.||.||...|.||.|||||.|||||.||.||.|
SEQ ID NO: 2    831  GAAGACCGGCTGGATTGAGATATTAGGGGCCGGAATGGTACATCCAAATG   880

SEQ ID NO: 1    881  TGCTGAAAATGGCCGGGTTCAATCCTGAAGAGTACCAGGGTTTTGGCTTC   930
                     ||.|||||.|||||.||||||.||.|||||||||.||.||.||.||.|||
SEQ ID NO: 2    881  TGTTGAAGATGGCTGGTTTCAACCCAGAAGAGTATCAAGGCTTCGGATTC   930

SEQ ID NO: 1    931  GGAATGGGTGTTGAACGTATCGCGATGCTGAAATACGGCATTGAAGATAT   980
                     ||.||||||.||.||||||.||.||||||.||.||.||.||.|||||.||
SEQ ID NO: 2    931  GGGATGGGGGTAGAGCGTATTGCAATGCTTAAGTATGGTATCGAAGACAT   980

SEQ ID NO: 1    981  CCGCCATTTCTATACCAATGATGTCAGATTCATTTCGCAGTTTAAACAGG  1030
                     .|||||||||||||.|||||.||..|.|||||||.|||||.||||||||
SEQ ID NO: 2    981  ACGCCATTTCTATACAAATGACGTTCGCTTCATTTCTCAGTTCAAACAGG  1030

SEQ ID NO: 1   1031  CGTAA   1035
                     |||||
SEQ ID NO: 2   1031  CGTAA   1035
```

PliaG_PheS(**CO)_TgyrA
LB+5mM 4CP

PliaG_PheS(CO)_TgyrA, PrpsF_PheS_TserOaroC
LB+5mM 4CP

SEQUENCE LISTING

```
<160> NUMBER OF SEQ ID NOS: 3

<210> SEQ ID NO 1
<211> LENGTH: 1035
<212> TYPE: DNA
<213> ORGANISM: Artificial Sequence
<220> FEATURE:
<223> OTHER INFORMATION: codon optimized PheS(**CO) counterselection
      marker

<400> SEQUENCE: 1
atggaagaga agcttaaaca gctcgaactg gaagctgcag aaaaagtaga agcggctggt        60
tcattaaaag aagttaacga tattcgggtg caatatctcg gaaaaaaagg gccgattaca      120
gaagttctcc gcggcatggg caaactgtcc gccgaagagc gcccgaaaat gggagccctc      180
gccaatgaag tgagagagcg cattgcagca gccataacgg cgaaaaatga acagcttgaa      240
caagaagaga tgaataaaaa actcagcagt cagacgattg atgtcacatt gcctggcagt      300
ccggtaaaca tcggcggacg ccatccgctg acggtcgtta ttgaagaaat tgaagattta      360
tttatcggta tgggatatac cgtagaagaa ggccctgaag tggaaacgga ttattataac      420
ttcgaagcgc tgaatctgcc gaaggaacat ccggcccgcg acatgcagga cagcttttac      480
attacagaag aaatgctgat gagaacgcag acgtcaccgg tgcagacacg cacgatggaa      540
aaacataaag gaaaaggccc cgtcaaaatc atttgtcccg gtaaagtgta tcgccgtgac      600
aacgatgacg cgacacattc ccatcagttc atgcagatcg agggtctcgt cgtggaccgc      660
aaaatcagca tgagcgacct gaaaggcacg cttgaattgg tcgcgaaaaa aatgttcggc      720
caagaccgtg aaatcaggct ccgtccgagc ttcttcccat tctccgagcc ttctgtcgaa      780
gtggatgtga cctgctttaa gtgcggcgga caaggctgct ccgtctgcaa aaaaacaggc      840
tggatcgaaa ttctcggcgc cggcatggtt cacccgaacg tgctgaaaat ggccgggttc      900
aatcctgaag agtaccaggg tttgcttc ggaatgggtg ttgaacgtat cgcgatgctg       960
aaatacggca ttgaagatat ccgccatttc tataccaatg atgtcagatt catttcgcag     1020
tttaaacagg cgtaa                                                       1035

<210> SEQ ID NO 2
<211> LENGTH: 1035
<212> TYPE: DNA
<213> ORGANISM: Artificial Sequence
<220> FEATURE:
<223> OTHER INFORMATION: codon optimized PheS(**) counterselection
      marker

<400> SEQUENCE: 2
atggaagaga aactcaaaca gcttgagctg gaagcagccg agaaagtaga ggcggcgggt        60
```

-continued

```
agcctcaaag aggtgaacga cattcgggta caatacctcg gtaagaaagg cccaataaca    120
gaagttttga gaggaatggg gaaactcagt gctgaggaga gaccgaaaat ggggcgctc     180 gccaacgaag ttcgggaaag aatcgcagca gctataaccg cgaaaaatga acaacttgaa    240
caagaagaaa tgaataagaa attgtcttct caaacgatcg acgttactct cccaggatca    300
ccggtcaata taggcgggag acatccgctc acggtcgtga tagaggaaat cgaagacctc    360
tttatcggga tgggttatac ggtggaagaa ggacctgagg tcgaaactga ttattacaat    420
ttcgaggctt taaatctgcc aaaagaacac cctgcgcggg atatgcagga ttcttttttac   480 atcacggagg agatgctcat gagaactcag actagtcctg tgcaaacgcg gacgatggaa    540
aagcacaaag gaaaggggcc tgtcaagatc atctgtccgg ggaaggtcta ccggcgggat    600
aacgacgacg cgactcatag tcatcaattc atgcaaattg agggcttggt agtggaccgt    660
aaaatttcca tgtctgattt gaagggggact cttgaattag ttgctaagaa aatgtttggt    720
caagacagag agatacgcct ccgcccatca tttttttccgt ttagtgagcc aagcgtagag   780
gtagatgtta cgtgcttcaa atgtggcggc caggggtgca gcgtgtgtaa gaagaccggc    840
tggattgaga tattagggggc cggaatggta catccaaatg tgttgaagat ggctggtttc    900
aacccagaag agtatcaagg cttcggattc gggatggggg tagagcgtat tgcaatgctt    960
aagtatggta tcgaagacat acgccatttc tatacaaatg acgttcgctt catttctcag    1020
ttcaaacagg cgtaa                                                     1035
```

<210> SEQ ID NO 3
<211> LENGTH: 344
<212> TYPE: PRT
<213> ORGANISM: Artificial Sequence
<220> FEATURE:
<223> OTHER INFORMATION: alpha-subunit of phenylalanyl-tRNA ligase
      (PheS) with A309G/T255S mutations

<400> SEQUENCE: 3

```
Met Glu Glu Lys Leu Lys Gln Leu Glu Leu Glu Ala Ala Glu Lys Val
1               5                   10                  15

Glu Ala Ala Gly Ser Leu Lys Glu Val Asn Asp Ile Arg Val Gln Tyr
            20                  25                  30

Leu Gly Lys Lys Gly Pro Ile Thr Glu Val Leu Arg Gly Met Gly Lys
        35                  40                  45

Leu Ser Ala Glu Glu Arg Pro Lys Met Gly Ala Leu Ala Asn Glu Val
    50                  55                  60

Arg Glu Arg Ile Ala Ala Ala Ile Thr Ala Lys Asn Glu Gln Leu Glu
65                  70                  75                  80

Gln Glu Glu Met Asn Lys Lys Leu Ser Ser Gln Thr Ile Asp Val Thr
                85                  90                  95

Leu Pro Gly Ser Pro Val Asn Ile Gly Gly Arg His Pro Leu Thr Val
            100                 105                 110

Val Ile Glu Glu Ile Glu Asp Leu Phe Ile Gly Met Gly Tyr Thr Val
        115                 120                 125

Glu Glu Gly Pro Glu Val Glu Thr Asp Tyr Tyr Asn Phe Glu Ala Leu
    130                 135                 140

Asn Leu Pro Lys Glu His Pro Ala Arg Asp Met Gln Asp Ser Phe Tyr
145                 150                 155                 160

Ile Thr Glu Glu Met Leu Met Arg Thr Gln Thr Ser Pro Val Gln Thr
                165                 170                 175

Arg Thr Met Glu Lys His Lys Gly Lys Gly Pro Val Lys Ile Ile Cys
```

-continued

```
                    180                 185                 190
Pro Gly Lys Val Tyr Arg Arg Asp Asn Asp Asp Ala Thr His Ser His
        195                 200                 205

Gln Phe Met Gln Ile Glu Gly Leu Val Val Asp Arg Lys Ile Ser Met
        210                 215                 220

Ser Asp Leu Lys Gly Thr Leu Glu Leu Val Ala Lys Lys Met Phe Gly
225                 230                 235                 240

Gln Asp Arg Glu Ile Arg Leu Arg Pro Ser Phe Phe Pro Phe Ser Glu
                245                 250                 255

Pro Ser Val Glu Val Asp Val Thr Cys Phe Lys Cys Gly Gly Gln Gly
                260                 265                 270

Cys Ser Val Cys Lys Lys Thr Gly Trp Ile Glu Ile Leu Gly Ala Gly
        275                 280                 285

Met Val His Pro Asn Val Leu Lys Met Ala Gly Phe Asn Pro Glu Glu
        290                 295                 300

Tyr Gln Gly Phe Gly Phe Gly Met Gly Val Glu Arg Ile Ala Met Leu
305                 310                 315                 320

Lys Tyr Gly Ile Glu Asp Ile Arg His Phe Tyr Thr Asn Asp Val Arg
                325                 330                 335

Phe Ile Ser Gln Phe Lys Gln Ala
                340
```

METHOD FOR COUNTERSELECTION IN MICROORGANISMS

CROSS-REFERENCE TO RELATED APPLICATIONS

This is application is a continuation of U.S. application Ser. No. 17/029,200 filed on Sep. 23, 2020, which claims the benefit of priority to U.S. Provisional Application No. 62/904,285 filed on Sep. 23, 2019, each of which is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_048_01US_SeqList_ST25. The text file of 6,448 bytes was created on Sep. 21, 2020, and is being submitted electronically via EFS-Web.

TECHNICAL FIELD

The present disclosure is directed to methods of scarless genomic engineering in microorganisms, such as *Bacillus*, and provides for new molecular tools and methods which enable scarless genetic editing using at least one counterselectable marker that has been codon optimized for the microorganism. The disclosure allows for the high-throughput introduction of stable genetic edits to a genome using either plasmid or linear DNA constructs for genetic engineering.

BACKGROUND

Previous work in *E. coli* has demonstrated that two mutations (A294G/T251A or A294G/T251S) to the sequence the α-subunit of phenylalanyl-tRNA ligase, PheS, can be used as a counterselectable marker due to the incorporation of 4-chloro-$_{DL}$-phenylalanine (4CP) in place of phenylalanine during translation, leading to cell death (Kast, Hennecke, 1991, Amino acid substrate specificity of *Escherichia coli* phenylalanyl-tRNA synthetase altered by distinct mutations, *J Mol Biol.* 222(1):99-124, Miyazaki, 2105, Molecular engineering of a PheS counterselection marker for improved operating efficiency in *Escherichia coli*, *Biotechniques,* 58(2):86-8). However, in *Bacillus* species those same PheS mutations are not effective.

When PheS sequences were aligned and the corresponding mutations, A309G/T255S, were identified and introduced into *B. subtilis* pheS, and expressed in *B. amyloliquefaciens* heterologously, this resulted in efficient killing in the presence of 4CP (Kharchenko M. S. et al., 2018. Improving the selection efficiency of the counter-selection marker pheS* for the genetic engineering of *Bacillus amyloliquefaciens*, *J Microbiol Methods,* 148:18-21, and Zhou, C. et al., 2017, pheS*, an effective host-genotype-independent counter-selectable marker for marker-free chromosome deletion in *Bacillus amyloliquefaciens*. *Appl Microbiol Biotechnol,* 101 (1):217-227). However, expression of the mutant gene in *B. subtilis* resulted in false-positive clones due to homologous recombination that replaced the mutant gene with the chromosomal wild-type pheS.

In the absence of an effective counterselectable marker, loop-out rates for *Bacillus* range from 0.8% to 5%, making the reliable construction of genomic edits very challenging, especially in a high-throughput (HTP) context. Although some effective counterselection markers have been reported in the literature for *Bacillus* species, many of those require pre-existing genetic mutations such as upp, which requires the native upp be deleted from the genome for counterselection with 5-fluorouracil (Dong and Zhang, 2014, Current development in genetic engineering strategies of *Bacillus* species, *Microb Cell Fact.* 13:63). Similarly, use of pyrF as a counterselection marker, requires that both pyrF and pyrR be deleted in the strain of interest. Thus, there is a need in the art for new molecular tools adapted to enable greater precision, efficiency, and predictability when editing the genome of *Bacillus*.

SUMMARY

In one embodiment, the disclosure teaches a high-throughput (HTP) method for generating at least one scarless genomic edit in a microorganism, comprising: providing a plasmid or linear DNA construct comprising a sequence of interest, a means for positive selection, and two counterselectable markers, wherein each of the counterselectable markers have been independently codon optimized for the microorganism and have a maximum tandem identity length of 500 base pairs when aligned with each other, and wherein each counterselectable marker is operably linked to at least one promoter; transforming the microorganism with the DNA construct; selecting for a microorganism strain having integrated the DNA construct based on the means for positive selection; selecting for a microorganism having undergone a homologous recombination event excising the backbone of the plasmid containing the counterselectable markers to produce a loop-out strain; screening the loop-out strain for the presence of the sequence of interest to produce a modified microorganism having at least one scarless genomic edit.

In another embodiment, the disclosure teaches a HTP method for generating at least one scarless genomic edit in a microorganism comprising providing a plasmid or linear DNA construct comprising a sequence of interest and at least one counterselectable marker, wherein the at least one counterselectable marker is a homolog of the α-subunit of Phenylalanyl-tRNA ligase, (PheS) that has been codon optimized for a microorganism, and further comprises homologous mutations corresponding to A309G/T255S of *Bacillus* PheS, and wherein the at least one counterselectable marker is operably linked to at least one promoter; transforming the microorganism with the DNA construct to produce a transformed strain; growing the transformed strain in the presence of 4-chlorphenylalanine to select for a strain having undergone a recombination event excising the backbone of the plasmid containing the at least one counterselectable marker to produce a loop-out strain; screening the loop-out strain for the presence of the sequence of interest to produce a scarless genetically modified microorganism. In another embodiment, the DNA construct comprises two counterselectable markers, wherein the markers have been independently codon optimized for the microorganism and are sufficiently distinct to prevent homologous recombination between the two markers.

In another embodiment, the present disclosure teaches a HTP method for generating at least one scarless genomic edit in a *Bacillus* species comprising providing a plasmid or linear DNA construct comprising a sequence of interest, a means for positive selection, and a counterselectable marker, wherein the counterselectable marker is an α-subunit of phenylalanyl-tRNA ligase, (PheS) that has been codon optimized for *Bacillus* and further comprises A309G/T255S mutations, and wherein the counterselectable marker is operably linked to at least one promoter; transforming a *Bacillus* species with the DNA construct; selecting a *Bacillus* strain having integrated the DNA construct based on the means for positive selection; growing the *Bacillus* strain having integrated the DNA construct in the presence of 4-chlorphenylalanine to select for a *Bacillus* strain having undergone a homologous recombination event excising the backbone of the plasmid containing the counterselectable marker to produce a loop-out strain; and screening the loop-out strain for the presence of the sequence of interest to produce a modified *Bacillus* strain having at least one scarless genomic edit.

In another embodiment, the dislosure provides for a method for generating at least one scarless genomic edit in a *Bacillus* species, comprising: providing a plasmid or linear DNA construct comprising a sequence of interest, a means for positive selection, and two counterselectable markers, wherein the counterselectable markers are an α-subunit of phenylalanyl-tRNA ligase, (PheS) that have been codon optimized for *Bacillus* and further comprise A309G/T255S mutations, wherein the counterselectable markers have a maximum tandem identity length of 500 base pairs when aligned with each other, and wherein each counterselectable marker is operably linked to at least one promoter; transforming a *Bacillus* species with the DNA construct; selecting for a *Bacillus* strain having integrated the DNA construct based on the means for positive selection; growing the *Bacillus* strain having integrated the DNA construct in the presence of 4-chlorphenylalanine to select for a *Bacillus* strain having undergone a homologous recombination event excising the backbone of the plasmid containing the counterselectable marker to produce a loop-out strain; and screening the loop-out strain for the presence of the sequence of interest to produce a modified *Bacillus* strain having at least one scarless genomic edit.

In some embodiments, the PheS that has been codon optimized for *Bacillus* is selected from the group consisting of SEQ ID NO: 1 (herein after referred to as PheS(CO)), or a sequence at least 90% identical thereto, and SEQ ID NO: 2 (herein after referred to as PheS (), or a sequence at least 75% identical thereto.

In some embodiments, the at least one promoter operably linked to the counterselectable marker is constitutive, inducible, differentially inducible, endogenous, heterologous, synthetic, a dual promoter, or a tandem promoter cluster. In some embodiments, the promoter is selected from the group consisting of PliaG, P43, PliaI, PrpsF, Pspac, and Pspank.

In some embodiments, the DNA construct further comprises a termination sequence. In some embodiments, the termination sequence is selected from the group consisting of TgyrA, Tsero_aroC, and TcodBA.

While it is contemplated that the methods can be applied to and/or utilized in any *Bacillus* species, in one embodiment, the *Bacillus* species is selected from the group consisting of *B. coagulans, B. ginsengihumi, B. shackletonii, B. aerius, B. aerophilus, B. stratosphericus, B. licheniformis, B. sonorensis, B. amyloliquefaciens, B. velezensis, B. atrophaeus, B. pumilus, B. safensis, B. altitudinis, B. vallismortis, B. subtilis, B. tequilensis, B. mojavensis, B. carboniphilus, B. oleronius, B. sporothermodurans, B. acidicola, B. aquimaris, B. vietnamensis, B. marisflavi, B. seohaeanensis, B. endophyticus*, and *B. humi*

While it is contemplated that the strain having integrated the DNA construct can be grown on or in media containing 4-chlorphenylalanine, in one embodiment the strain is grown on or in media containing between 1 mM and 20 mM 4-chlorphenylalanine.

While it is contemplated that a number of screening methods can be used with the methods disclosed herein, in one embodiment the screening of the loop-out strain comprises sequencing, DNA fingerprinting, or phenotypic analysis.

In some embodiments, the sequence of interest is an endogenous gene, wherein the endogenous gene has at least one mutation sequence, or a heterologous gene. In some embodiments, the mutation sequence comprises a mutation selected from the group consisting of: a single nucleotide insertion, an insertion of two or more nucleotides, an insertion of a nucleic acid sequence encoding one or more proteins, a single nucleotide deletion, a deletion of two or more nucleotides, a deletion of one or more coding sequences, a substitution of a single nucleotide, a substitution of two or more nucleotides, two or more non-contiguous insertions, deletions, and/or substitutions, and any combination thereof.

In some embodiments, the disclosure provides for a genetically modified *Bacillus* strain produced by the methods disclosed herein. In some embodiments, the modified *Bacillus* strain produced is subjected to further genetic modification.

In some embodiments, the present disclosure provides for a DNA construct comprising at least one of a counterselectable marker comprising SEQ ID NO: 1, or a sequence at least 90% identical thereto, and a counterselectable marker comprising SEQ ID NO: 2, or a sequence at least 75% identical thereto.

In some embodiments, the present disclosure provides for an isolated nucleic acid comprising SEQ ID NO: 1, or a sequence at least 90% identical thereto, or SEQ ID NO: 2, or a sequence at least 75% identical thereto.

BRIEF DESCRIPTION OF THE DRAWINGS

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 5 is a nucleotide sequence alignment from EMBL-EBI, (EMBOSS Water, Smith-Waterman algorithm) between SEQ ID NO: 1 (PheS(CO)) and SEQ ID NO: 2 (PheS()).

DEFINITIONS

Figure 1A:
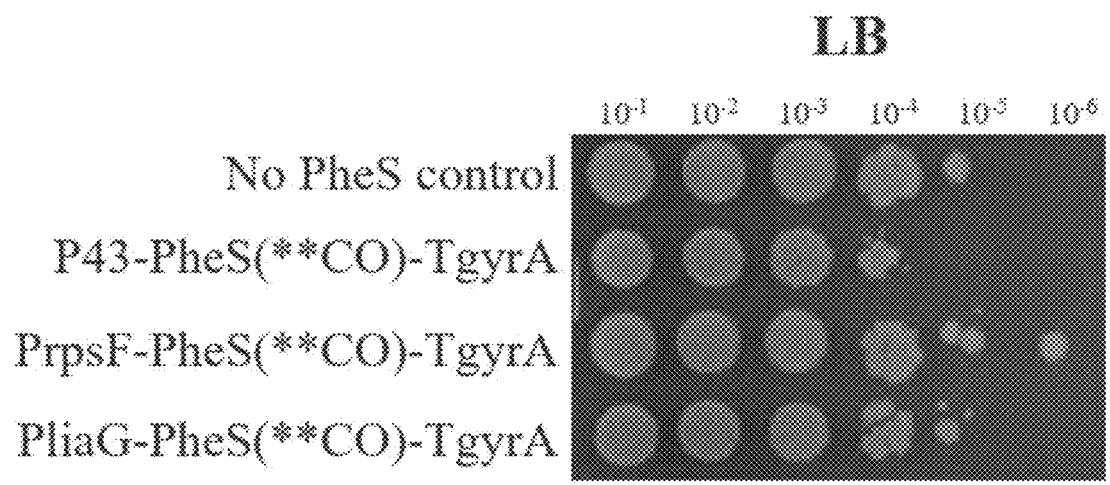
FIG. 1A-FIG. 1D show photographs of a culture dilution series of *B. subtilis* strain S30A transformed with plasmids bearing PheS(**CO) driven by different promoters. Cultures were plated on lysogeny broth (LB) alone (FIG. 1A), selective antibiotic (chloramphenicol [Chlor]) (FIG. 1B), counterselection reagent 4CP (FIG. 1C), or the combination of both (FIG. 1D).
Figure 1B:
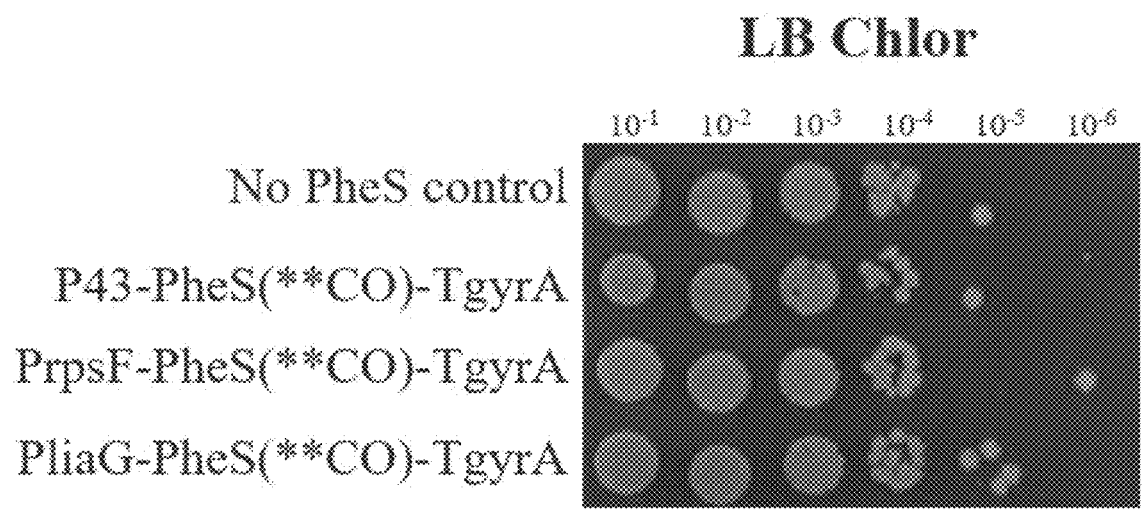

While the following terms are believed to be well understood by one of ordinary skill in the art, the following definitions are set forth to facilitate explanation of the presently disclosed subject matter.

The term "a" or "an" refers to one or more of that entity, i.e., can refer to a plural referent. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% (i.e., within 10%, 9%, 8%, 7%, 6%, 5%, 4%, 3%, 2%, 1%, or less) above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

A "clone" is a population of cells derived from a single cell or common ancestor by mitosis. A "cell line" is a clone of a primary cell that is capable of stable growth in vitro for many generations.

As used herein, the term "codon optimization" refers to a genetic engineering method wherein the codon bias of the host organism is used to generate synonymous codon changes in a recombinant gene to increase expression and translation of the recombinant gene in the host.

The term "competent cell" refers to a cell which has the ability to take up and replicate an exogenous nucleic acid.

As used herein, "counterselectable marker" or a "counterselection marker" is a nucleic acid segment that eliminates or inhibits growth of a host organism upon selection. For example, it may render the cells sensitive to one or more chemicals/growth conditions/genetic backgrounds.

As used herein, the term "endogenous" or "endogenous gene," refers to the natural sequence and/or location of a gene. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system. Artificially mutated variants of endogenous genes are considered "exogenous" for the purposes of this disclosure.

As used herein, an "extra-chromosomally replicating plasmid" is an autonomously replicating vector that exists as an extra-chromosomal entity. The replication of an extra-chromosomally replicating plasmid is independent of chromosomal replication.

The term "genetic modification" or "mutation" refers to any alteration of DNA. Representative gene modifications include a "nucleotide change" such as insertions, deletions, substitutions, and combinations thereof, and can be as small as a single base or as large as tens of thousands of bases. In some cases, mutations contain alterations that produce silent substitutions, additions, or deletions, but do not alter the properties or activities of the encoded protein or how the proteins are made. The term "genetic modification" also encompasses inversions of a nucleotide sequence and other chromosomal rearrangements, whereby the position or orientation of DNA comprising a region of a chromosome is altered. A chromosomal rearrangement can comprise an intrachromosomal rearrangement or an interchromosomal rearrangement.

As used herein, the term "heterologous" refers to an amino acid or a nucleic acid sequence (e.g., gene or promoter), which is not naturally found in the particular organism or is not naturally found in a particular context (e.g., genomic or plasmid location) in the particular organism.

A "high-throughput (HTP)" method of genomic engineering may involve the utilization of at least one piece of automated equipment (e.g. a liquid handler or plate handler machine) to carry out at least one step of the method.

As used herein, the term "homologous" or "homologue" encompasses orthologs and paralogs and refers to related sequences that share a common ancestor or family member and are determined based on the degree of sequence identity. "Homologous sequences" or "homologs" may also be functionally related. A functional relationship may be indicated in any one of a number of ways, including, but not limited to: (a) degree of sequence identity and/or (b) the same or similar biological function. Homology can be determined using software programs readily available in the art, such as NCBI BLAST® (Basic Local Alignment Search Tool), using default parameters, or using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule.

As used herein, the phrases "DNA construct", "expression cassette", "chimeric construct", "construct", and "recombinant DNA construct" are used interchangeably herein. A recombinant DNA construct comprises an artificial combination of nucleic acid fragments, e.g., regulatory and coding sequences that are not found together in nature. For example, a construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used.

The term "operably linked" refers to the juxtaposition of two or more components (such as sequence elements) having a functional relationship. For example, the sequential arrangement of the promoter polynucleotide with a further oligo- or polynucleotide, resulting in transcription of the further polynucleotide.

The term "product of interest" or "biomolecule" as used herein refers to any product produced by microbes. In some cases, the product of interest may be a small molecule, enzyme, peptide, amino acid, organic acid, synthetic compound, fuel, alcohol, etc. For example, the product of interest or biomolecule may be any primary or secondary extracellular metabolite.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter.

As used herein, "selectable marker" is a nucleic acid segment that allows one to select for a molecule (e.g., a plasmid) or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

A cell has been "transformed" or "transfected" when exogenous DNA has been introduced inside the cell. The presence of the exogenous DNA results in permanent or transient genetic change.

As used herein, the phrase "scarless" refers to a method of genetic engineering, also known as "scarless genomic editing" or "scarless gene replacement" wherein any markers (selectable and/or counterselectable) are removed, for example by recombination, from the transformed microorganism. Scarless may also be referred to as "clean" or "unmarked" mutations.

DETAILED DESCRIPTION

The following description includes information that may be useful in understanding the present disclosure. It is not an admission that any of the information provided herein is prior art or relevant to the presently claimed disclosures, or that any publication specifically or implicitly referenced is prior art.

Overview

The disclosure provides for new molecular tools and methods, which enable scarless genetic editing in a microorganism. The methods of selection and counter selection, in combination with homologous recombination events, are used to generate scarless mutations in a microorganism in a two-step process. In the first step, a DNA cassette (or DNA construct) containing sequence of interest (SOI), a means for positive selection, and counterselection marker (CSM) is introduced in the host genome. The means for positive selection permits the selection of cells that have incorporated the cassette. In a second step, the action of the CSM exerts a negative pressure favoring a second homologous recombination event (loop-out) that results in a scarless mutation.

An embodiment of the present disclosure teaches a HTP method for generating at least one scarless genomic edit in a microorganism, comprising: providing a plasmid or linear DNA construct comprising a sequence of interest, a means for positive selection, and two counterselectable markers, wherein each of the counterselectable markers has been independently codon optimized for the microorganism and have a maximum tandem identity length of 500 base pairs when aligned with each other, and wherein each counterselectable marker is operably linked to at least one promoter; transforming the microorganism with the DNA construct; selecting for a microorganism strain having integrated the DNA construct based on the means for positive selection; selecting for a microorganism having undergone a homologous recombination event excising the backbone of the plasmid containing the counterselectable markers to produce a loop-out strain; screening the loop-out strain for the presence of the sequence of interest to produce a modified microorganism having at least one scarless genomic edit.

In another embodiment, the disclosure teaches a HTP method for generating at least one scarless genomic edit in a microorganism comprising providing a plasmid or linear DNA construct comprising a sequence of interest and at least one counterselectable marker, wherein the at least one counterselectable marker is a homolog of the α-subunit of Phenylalanyl-tRNA ligase, (PheS) that has been codon optimized for a microorganism, and further comprises homologous mutations corresponding to A309G/T255S of Bacillus PheS, and wherein the at least one counterselectable marker is operably linked to at least one promoter; transforming the microorganism with the DNA construct to produce a transformed strain; growing the transformed strain in the presence of 4-chlorphenylalanine to select for a strain having undergone a recombination event excising the backbone of the plasmid containing the at least one counterselectable marker to produce a loop-out strain; and screening the loop-out strain for the presence of the sequence of interest to produce a scarless genetically modified microorganism.

In addition to the PheS counterselectable marker described further below, other examples of such counterselectable marker genes include sacB, rpsL(strA), tetAR, pheS, thyA, gata-1, or ccdB, the function of which is described in Reyrat et al. 1998 "Counterselectable Markers: Untapped Tools for Bacterial Genetics and Pathogenesis." *Infect Immun.*, 66(9): 4011-4017.

Microorganisms suitable for the methods disclosed herein include, but are not limited to, bacterial cells, algal cells, plant cells, fungal cells, insect cells, and mammalian cells. As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists.

Codon Optimization

Protein expression is governed by a host of factors including those that affect transcription, mRNA processing, and stability and initiation of translation. Optimization can thus address any of a number of sequence features of any particular gene. Translation may be paused due to the presence of codons in the polynucleotide of interest that are rarely used in the host organism, and this may have a negative effect on protein translation due to their scarcity in the available tRNA pool. Specifically, it can result in reduced protein expression.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

The optimization process can begin, for example, by identifying the desired amino acid sequence to be expressed by the host. From the amino acid sequence, a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

Optimized coding sequences containing codons preferred by a particular prokaryotic or eukaryotic host (see also, Murray et al. (1989) *Nucl. Acids Res.* 17:477-508) can be prepared, for example, to increase the rate of translation or to produce recombinant RNA transcripts having desirable properties, such as a longer half-life, as compared with transcripts produced from a non-optimized sequence.

In another embodiment, the disclosure teaches a DNA construct comprising two counterselectable markers, wherein the markers have been independently codon optimized for the microorganism and are sufficiently distinct to prevent homologous recombination between the two markers. In some embodiments, the markers have a maximum tandem identity length of 500 base pairs when aligned with each other. In other embodiments, the markers have a maximum tandem identity length of 250 base pairs when aligned with each other. In other embodiments, the markers have a maximum tandem identity length of 100 base pairs when aligned with each other. In other embodiments, the markers have a maximum tandem identity length of 25 base pairs when aligned with each other. See for example, Koren, P. et al., (2000), Influence of homology size and polymorphism on plasmid integration in the yeast CYC1 DNA region. *Current Genetics.* 37. 292-297.

Phenylalanyl-tRNA Synthetase

Phenylalanyl-tRNA synthetase is an enzyme that catalyzes the aminoacylation of tRNA$^{Phe}$ with Phenylalanine. This "charging" or "loading" of the correct amino acid with its corresponding tRNA is an important part of translation and the synthesis of proteins. Previous work in *E. coli* has demonstrated that two mutations (A294G/T251A or A294G/T251S) to the sequence the α-subunit of phenylalanyl-tRNA ligase, PheS, can be used as a counterselectable marker due to the incorporation of 4-chloro-DL-phenylalanine (4CP) in place of phenylalanine during translation, leading to cell death (Kast, Hennecke, 1991, Amino acid substrate specificity of *Escherichia coli* phenylalanyl-tRNA synthetase altered by distinct mutations, *J Mol Biol.* 222(1):99-124, Miyazaki, 2105, Molecular engineering of a PheS counter-selection marker for improved operating efficiency in *Escherichia coli, Biotechniques,* 58(2):86-8). However, in *Bacillus* species those same PheS mutations are not effective.

When PheS sequences were aligned and the corresponding mutations, A309G/T255S, were identified and introduced into *B. subtilis* pheS, and expressed in *B. amyloliquefaciens* heterologously, this resulted in efficient killing in the presence of 4CP (Kharchenko M. S. et al., 2018. Improving the selection efficiency of the counter-selection marker pheS* for the genetic engineering of *Bacillus amyloliquefaciens, J Microbiol Methods.* 148:18-21, and Zhou, C. et al., 2017, pheS *, an effective host-genotype-independent counter-selectable marker for marker-free chromosome deletion in *Bacillus amyloliquefaciens. Appl Microbiol Biotechnol.;* 101(1):217-227).

In the absence of effective counterselectable marker, loop-out rates for *Bacillus* range from 0.8% to 5%, making the reliable construction of genomic edits very challenging, especially in a high-throughput (HTP) context. Although some effective counterselection markers have been reported in the literature for *Bacillus* species, many of those require pre-existing genetic mutations such as upp, which requires the native upp be deleted from the genome for counterselection with 5-fluorouracil. Similarly, use of pyrF as a counterselection marker, requires that both pyrF and pyrR be deleted in the strain of interest (Dong and Zhang 2014, Current development in genetic engineering strategies of *Bacillus* species, *Microb Cell Fact.* 13:63). However, expression of the mutant gene in *B. subtilis* resulted in false-positive clones due to homologous recombination that replaced the mutant gene with the chromosomal wild-type pheS.

One embodiment of the disclosure provides for a HTP method for generating at least one scarless genomic edit in a *Bacillus* species. Methods for optimizing codons to improve expression in various hosts are known in the art and described above (see also U.S. Pat. App. Pub. No. 2007/0292918, incorporated herein by reference in its entirety). This allows for the introduction of stable genetic edits to the *Bacillus* genome using either plasmid or linear DNA constructs for genetic engineering. The counterselection marker disclosed herein provides high efficiency genetic editing in *Bacillus* species, with PheS**CO leading to cell death solely in the presence of 4-chlorophenylalanine. While the methods disclosed herein have been successfully demonstrated to be effective in *B. licheniformis*, and multiple strains of *B. subtilis* for the construction of scarless genomic edits, one skilled in the art will recognize they are applicable to all *Bacillus* species.

In an embodiment of the present disclosure, a plasmid or linear DNA construct is provided comprising a sequence of interest, a means for positive selection, and a counterselectable marker, wherein the counterselectable marker is an α-subunit of Phenylalanyl-tRNA ligase, (PheS) that has been codon optimized for *Bacillus* and further comprises A309G/T255S mutations, and wherein the counterselectable marker is operably linked to at least one promoter; transforming a *Bacillus* species with the DNA construct; selecting for a *Bacillus* strain having integrated the DNA construct based on the means for positive selection; growing the *Bacillus* strain having integrated the DNA construct in the presence of 4-chlorophenylalanine to select for a *Bacillus* strain having undergone a homologous recombination event excising the backbone of the plasmid containing the counterselectable marker to produce a loop-out strain; and screening the loop-out strain for the presence of the sequence of interest to produce a modified *Bacillus* strain having at least one scarless genomic edit.

For the codon optimization of PheS(**CO), the *Bacillus amyloliquefaciens* PheS sequence was used so the sequence is naturally codon optimized for *Bacillus* species. For the codon optimization of PheS(**), SEQ ID NO: 3 was input to the Integrated DNA Technologies (IDT) Codon Optimization Tool for optimization to *B. subtilis*.

In another embodiment, the PheS that has been codon optimized comprises SEQ ID NO: 1 (PheS(CO), or a sequence at least 90% identical thereto. In another embodiment, the PheS that has been codon optimized comprises SEQ ID NO: 2 (PheS(), or a sequence at least 75% identical thereto. Isolated nucleic acids and DNA constructs comprising these sequences are also embodiments of the present disclosure.

In another embodiment, strains having integrated the DNA constructs comprising the PheS counterselectable marker are grown on or in media containing between 1 mM and 20 mM 4-chlorphenyl alanine.

*Bacillus* Species

*Bacillus* is a genus of Gram-positive or Gram-variable spore-forming, aerobic or facultative anaerobic, rod-shaped bacteria. They are ubiquitous in nature and have a wide range of physiologic characteristics and the ability to produce a variety of enzymes, antibiotics and metabolites, making them useful as a model organism and in many different industries, including for example, the medical, pharmaceutical, agricultural, and food industries. Non-limiting examples of *Bacillus* that may be used with the methods disclosed herein include species of *B. acidicele, B. acidicola, B. acidiproducens, B. acidocaldarius, B. acidoterrestris, B. aeolius, B. aerius, B. aerophilus, B. agaradhaerens, B. agri, B. aidingensis, B. akibai, B. alcalophilus, B. algicola, B. alginolyticus, B. alkalidiazotrophicus, B. alkalinitrilicus, B. alkalisediminis, B. alkalitelluris, B. altitudinis, B. alveayuensis, B. alvei, B. amyloliquefaciens,* B. a. subsp. *amyloliquefaciens,* B. a. subsp. *Plantarum, B. aminovorans, B. amylolyticus, B. andreesenii, B. aneurinilyticus, B. anthracis, B. aquimaris, B. arenosi, B. arseniciselenatis, B. arsenicus, B. aurantiacus, B. arvi, B. aryabhattai, B. asahii, B. atrophaeus, B. axarquiensis, B. azotofixans, B. azotoformans, B. badius, B. barbaricus, B. bataviensis, B. beijingensis, B. benzoevorans, B. beringensis, B. berkeleyi, B. beveridgei, B. bogoriensis, B. boroniphilus, B. borstelensis, B. brevis Migula, B. butanolivorans, B. canaveralius, B. carboniphilus, B. cecembensis, B. cellulosilyticus, B. centrosporus, B. cereus, B. chagannorensis, B. chitinolyticus, B. chondroitinus, B. choshinensis, B. chungangensis, B. cibi, B. circulans, B. clarkia, B. clausii, B. coagulans, B. coahuilensis, B. cohnii, B. composti, B. curdlanolyticus, B. cycloheptanicus, B. cytotoxicus, B. daliensis, B. decisifrondis, B. decolorationis, B. deserti, B. dipsosauri, B. drentensis, B. edaphicus, B. ehimensis, B. eiseniae, B. enclensis, B. endophyticus, B. endoradicis, B. farraginis, B. fastidiosus, B. fengqiuensis, B. firmus, B. flexus, B. foraminis, B. fordii, B. formosus, B. fortis, B. fitmarioli, B. funiculus, B. fusiformis, B. galactophilus, B. galactosidilyticus, B. galliciensis, B. gelatini, B. gibsonii, B. ginseng, B. ginsengihumi, B. ginsengisoli, B. glucanolyticus, B. gordonae, B. gottheilii, B. graminis, B. halmapalus, B. haloalkaliphilus, B. halochares, B. halodenitrificans, B. halodurans, B. halophilus, B. halosaccharovorans, B. hemicellulosilyticus, B. hemicentroti, B. herbersteinensis, B. horikoshii, B. horneckiae, B. horti, B. huizhouensis, B. humi, B. hwajinpoensis, B. idriensis, B. indicus, B. infantis, B. infernus, B. insolitus, B. invictae, B. iranensis, B. isabeliae, B. isronensis, B. jeotgali, B. kaustophilus, B. kobensis, B. kochii, B. kokeshiiformis, B. koreensis, B. korlensis, B. kribbensis, B. krulwichiae, B. laevolacticus, B. larvae, B. laterosporus, B. lautus, B. lehensis, B. lentimorbus, B. lentus, B. licheniformis, B. ligniniphilus, B. litoralis, B. locisalis, B. luciferensis, B. luteolus, B. luteus, B. macauensis, B. macerans, B. macquariensis, B. macyae, B. malacitensis, B. mannanilyticus, B. marisflavi, B. marismortui, B. marmarensis, B. massiliensis, B. megaterium, B. mesonae, B. methanolicus, B. methylotrophicus, B. migulanus, B. mojavensis, B. mucilaginosus, B. muralis, B. murimartini, B. mycoides, B. naganoensis, B. nanhaiensis, B. nanhaiisediminis, B. nealsonii, B. neidei, B. neizhouensis, B. niabensis, B. niacin, B.* novalis, *B. oceanisediminis*, *B. odyssey*, *B. okhensis*, *B. okuhidensis*, *B. oleronius*, *B. oryzaecorticis*, *B. oshimensis*, *B. pabuli*, *B. pakistanensis*, *B. pallidus*, *B. pallidus*, *B. panacisoli*, *B. panaciterrae*, *B. pantothenticus*, *B. parabrevis*, *B. paraflexus*, *B. pasteurii*, *B. patagoniensis*, *B. peoriae*, *B. persepolensis*, *B. persicus*, *B. pervagus*, *B. plakortidis*, *B. pocheonensis*, *B. polygoni*, *B. polymyxa*, *B. popilliae*, *B. pseudalcalophilus*, *B. pseudofirmus*, *B. pseudomycoides*, *B. psychrodurans*, *B. psychrophilus*, *B. psychrosaccharolyticus*, *B. psychrotolerans*, *B. pulvifaciens*, *B. pumilus*, *B. purgationiresistens*, *B. pycnus*, *B. qingdaonensis*, *B. qingshengii*, *B. reuszeri*, *B. rhizosphaerae*, *B. rigui*, *B. ruris*, *B. safensis*, *B. salaries*, *B. salexigens*, *B. saliphilus*, *B. schlegelii*, *B. sediminis*, *B. selenatarsenatis*, *B. selenitireducens*, *B. seohaeanensis*, *B. shacheensis*, *B. shackletonii*, *B. siamensis*, *B. silvestris*, *B. simplex*, *B. spiralis*, *B. smithii*, *B. soli*, *B. solimangrovi*, *B. solisalsi*, *B. songklensis*, *B. sonorensis*, *B. sphaericus*, *B. sporothermodurans*, *B. stearothermophilus*, *B. stratosphericus*, *B. subterraneus*, *B. subtilis*, *B. s. subsp. Inaquosorum*, *B. s. subsp. Spizizenii*, *B. s. subsp. Subtilis*, *B. taeanensis*, *B. tequilensis*, *B. thermantarcticus*, *B. thermoaerophilus*, *B. thermoamylovorans*, *B. thermocatenulatus*, *B. thermocloacae*, *B. thermocopriae*, *B. thermodenitrificans*, *B. thermoglucosidasius*, *B. thermolactis*, *B. thermoleovorans*, *B. thermophilus*, *B. thermoruber*, *B. thermosphaericus*, *B. thiaminolyticus*, *B. thioparans*, *B. thuringiensis*, *B. tianshenii*, *B. trypoxylicola*, *B. tusciae*, *B. Validus*, *B. vallismortis*, *B. vedderi*, *B. velezensis*, *B. vietnamensis*, *B. vireti*, *B. vulcani*, *B. wakoensis*, *B. xiamenensis*, *B. xiaoxiensis*, and *B. zhanjiangensis*.

Data suggests that *Bacillus* species may be sub-grouped based on 16S rDNA sequencing (Wei Wang MS. Phylogenetic relationships between *Bacillus* species and related genera inferred from 16s rDNA sequences. *Braz J Microbiol*. 2009; 40(3):505-521). Thus, in another embodiment, the methods of scarless genomic editing disclosed herein may be used with a *Bacillus* species selected from the group consisting of *B. coagulans*, *B. ginsengihumi*, *B. shackletonii*, *B. aerius*, *B. aerophilus*, *B. stratosphericus*, *B. licheniformis*, *B. sonorensis*, *B. amyloliquefaciens*, *B. velezensis*, *B. atrophaeus*, *B. pumilus*, *B. safensis*, *B. altitudinis*, *B. vallismortis*, *B. subtilis*, *B. tequilensis*, *B. mojavensis*, *B. carboniphilus*, *B. oleronius*, *B. sporothermodurans*, *B. acidicola*, *B. aquimaris*, *B. vietnamensis*, *B. marisflavi*, *B. seohaeanensis*, *B. endophyticus*, and *B. humi*.

Assembling & Cloning DNA Constructs

As will be understood by one skilled in the art, the methods of generating scarless genomic edits disclosed herein may be used with any genetic editing technology involving transformation of cells with exogenous DNA. In some embodiments, the present disclosure teaches methods for constructing vectors capable of inserting a sequence of interest (e.g. containing a particular heterologous gene or a mutation to an endogenous gene) into the genome of host organisms. In some embodiments, the present disclosure teaches methods of cloning vectors comprising the target DNA, homology arms, and at least one selection marker.

In some embodiments, the present disclosure is compatible with any vector suited for transformation into the host organism. In certain instances, the target DNA can be inserted into vectors, constructs or plasmids obtainable from any repository or catalogue product, such as a commercial vector (see e.g., DNA2.0 custom or GATEWAY® vectors).

In some embodiments, the methods of scarless genomic editing disclosed herein may employ an assembly/cloning method. Examples of assembly/cloning methods include: i) type II conventional cloning, ii) type II S-mediated or "Golden Gate" cloning (see, e.g., Engler, C., R. Kandzia, and S. Marillonnet. 2008 "A one pot, one step, precision cloning method with high-throughput capability". *PLos One* 3:e3647; Kotera, I., and T. Nagai. 2008 "A high-throughput and single-tube recombination of crude PCR products using a DNA polymerase inhibitor and type IIS restriction enzyme." *J Biotechnol* 137:1-7.; Weber, E., R. Gruetzner, S. Werner, C. Engler, and S. Marillonnet. 2011 Assembly of Designer TAL Effectors by Golden Gate Cloning. *PloS One* 6:e19722), iii) GATEWAY® recombination, iv) TOPO® cloning, exonuclease-mediated assembly (Aslanidis and de Jong 1990. "Ligation-independent cloning of PCR products (LIC-PCR)." *Nucleic Acids Research*, Vol. 18, No. 20 6069), v) homologous recombination, vi) non-homologous end joining, vii) Gibson assembly (Gibson et al., 2009 "Enzymatic assembly of DNA molecules up to several hundred kilobases" *Nature Methods* 6, 343-345) or a combination thereof. Modular type IIS based assembly strategies are disclosed in PCT Publication WO 2011/154147, the disclosure of which is incorporated herein by reference.

Methods for Gene Editing

The disclosure provides methods for scarless gene editing, wherein a sequence of interest is inserted into the host genome. As will be understood by one skilled in the art, the sequence of interest may be an endogenous gene that has been edited or it may be a heterologous gene. In some embodiments, the present disclosure teaches methods for gene editing by introducing, deleting, or replacing selected portions of genomic DNA. Gene editing (or mutations) may include single nucleotide insertions or deletions, insertions or deletions of two or more nucleotides, insertion of a sequence encoding one or more proteins, a deletion of a sequence encoding one or more proteins, substitution of a single nucleotide, or substitution of two or more nucleotides.

In other embodiments, the present disclosure teaches mutating selected DNA regions outside of the host organism, and then inserting the mutated sequence back into the host organism. For example, in some embodiments, the present disclosure teaches mutating native or synthetic promoters to produce a range of promoter variants with various expression properties. In other embodiments, the present disclosure is compatible with single gene optimization techniques, such as ProSAR (Fox et al. 2007. "Improving catalytic function by ProSAR-driven enzyme evolution." *Nature Biotechnology* Vol 25 (3) 338-343, incorporated by reference herein).

In some embodiments, the selected regions of DNA are produced in vitro via gene shuffling of natural variants, or shuffling with synthetic oligos, plasmid-plasmid recombination, virus plasmid recombination, virus-virus recombination. In other embodiments, the genomic regions are produced via error-prone PCR.

In some embodiments, generating mutations in selected genetic regions is accomplished by "reassembly PCR." Briefly, oligonucleotide primers (oligos) are synthesized for PCR amplification of segments of a nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols. In brief, in an assembly protocol, the PCR products are first purified away from the primers, by, for example, gel electrophoresis or size exclusion chromatography. Purified products are mixed together and subjected to about 1-10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments of the disclosure, mutated DNA regions, such as those discussed above, are enriched for mutant sequences so that the multiple mutant spectrum, i.e. possible combinations of mutations, is more efficiently sampled. In some embodiments, mutated sequences are identified via a mutS protein affinity matrix (Wagner et al., *Nucleic Acids Res.* 23(19):3944-3948 (1995); Su et al., *Proc. Natl. Acad. Sci.* (U.S.A.), 83:5057-5061 (1986)) with a preferred step of amplifying the affinity-purified material in vitro prior to an assembly reaction. This amplified material is then put into an assembly or reassembly PCR reaction as described in later portions of this application.

Thus, in some embodiments, "mutagenesis" or "genetic modification as used herein comprises all techniques known in the art for inducing mutations, including error-prone PCR mutagenesis, oligonucleotide-directed mutagenesis, site-directed mutagenesis, and iterative sequence recombination by any of the techniques described herein.

Selectable Marker Gene

Selectable markers may be used with the methods of the present disclosure as a means for positive selection of transformants. The selection marker may produce a RNA, peptide, or protein, or can provide a binding site for RNA, peptides, proteins, inorganic and organic compounds or compositions and the like. Examples of selectable markers include but are not limited to: (1) nucleic acid segments that encode products which provide resistance against otherwise toxic compounds (e.g., antibiotics such as ampicillin, kanamycin, tetracycline, chloramphenicol, zeocin, streptomycin); (2) nucleic acid segments that encode products which are otherwise lacking in the recipient cell (e.g., tRNA genes, auxotrophic markers); (3) nucleic acid segments that encode products which suppress the activity of a gene product; (4) nucleic acid segments that encode products which can be readily identified (e.g., phenotypic markers such as β-galactosidase, green fluorescent protein (GFP), yellow fluorescent protein (YFP), cyan fluorescent protein (CFP), and cell surface proteins); (5) nucleic acid segments that encode products that bind other products which are otherwise detrimental to cell survival and/or function; (6) nucleic acid segments that encode nucleic acids that otherwise inhibit the activity of any of the nucleic acid segments resulting in a visible or selectable phenotype (e.g., antisense oligonucleotides); (7) nucleic acid segments that encode products that bind other products that modify a substrate (e.g. restriction endonucleases); (8) nucleic acid segments that can be used to isolate or identify a desired molecule (e.g. specific protein binding sites); (9) nucleic acid segments that encode a specific nucleotide sequence which can be otherwise non-functional (e.g., for PCR amplification of subpopulations of molecules); and (10) nucleic acid segments, which when absent, directly or indirectly confer resistance or sensitivity to particular compounds.

In some embodiments, the selectable marker is an antibiotic resistance gene, for example, a chloramphenicol resistance gene, an ampicillin resistance gene, a tetracycline resistance gene, a zeocin resistance gene, a spectinomycin resistance gene a kanamycin resistance gene, a tetracycline resistance gene, a neomycin resistance gene, a vancomycin resistance gene, a methicillin resistance gene, a penicillin resistance gene, an oxacillin resistance gene, erythromycin an erythromycin resistance gene, a linezolid resistance gene, a puromycin resistance gene, or a hygromycin resistance gene.

Non-limiting examples of selective agents include antibiotics, such as ampicillin, tetracyclin, zeocin, spectinomycin, kanamycin, neomycin, vancomycin, methicillin, oxacillin, erythromycin, linezolid, puromycin, and hygromycin. Non-limiting examples of selectable marker genes include pyrG, hph, nat, amdS, nptII, niaD, and argB.

Promoters

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

In some embodiments, the at least one promoter operably linked to the counterselectable marker is constitutive, inducible, differentially inducible, endogenous, heterologous, synthetic, a dual promoter, or a tandem promoter cluster.

In some embodiments, the methods of scarless genomic editing disclosed herein may be used with various promoters, including, for example, PliaG, P43, PliaI, PrpsF, Pspac, and P spank (Vagner et al., 1998 November. A vector for systematic gene inactivation in *Bacillus subtilis*. *Microbiology* 144 (Pt 11), 3097-3104, Wu et al., 1991 Engineering a *Bacillus subtilis* expression-secretion system with a strain deficient in 6 extracellular proteases. *J. Bacteriol.* 173, 4952-4958). Other promoters include, for example, Plaps (Yang et al., 2013 Generation of an artificial double promoter for protein expression in *Bacillus subtilis* through a promoter trap system. *PLoS ONE* 8:e56321), PBL$_9$ (Geng et al., 2014 Mining tissue-specific contigs from peanut (*Arachis hypogaea* L.) for promoter cloning by deep transcriptome sequencing. *Plant Cell Physiol.* 55, 1793-1801), Phag, PtufA, PcapD, PyqeY, PsodA, PfusA, PgapA, PahpF, PglnA, PamyE, and Pmdh (Meng F. et al., Enhanced Expression of Pullulanese in *Bacillus subtilis* by New Strong Promoters Mined from Transcriptome Data, both Alone and in Combination, *Microbiol.*, November 2018).

Where more than one counterselectable marker is used, embodiments herein include each counterselectable marker having a distinct operably linked promoter.

In some embodiments, dual promoters and/or promoter cassettes (tandem promoter clusters) may be used with the methods disclosed herein, such as, for example, PhpaII-PamyQ (Zhang et al., 2017 High-level extracellular protein production in *Bacillus subtilis* using an optimized dual-promoter expression system. *Microb. Cell Fact.* 16:32), PgsiB-PHpaII (Guan C. R., et al, 2016 Construction of a highly active secretory expression system via an engineered dual promoter and a highly efficient signal peptide in *Bacillus subtilis*. *N. Biotechnol.* 33, 372-379), PsodA+hag, PsodA+tugA, PsodA+fusA, PsodA+amyE, Phag+tufa, Phag+fusA, Phag+amyE, PtufA+fusA, PtufA+amyE, PfusA+amyE, PsodA+sodA, Phag+hag, PtufA+tufA, PfusA+fusA, PamyE+amyE, PsodA+hag+tufa, PsodA+hag+fusA, PsodA+hag+amyE, PsodA+tufA+fusA, PsodA+tufA+amyE, PsodA+fusA+amyE, Phag+tufA+fusA, Phag+tufA+amyE, Phag+fusA+amyE, PtufA+fusA+amyE, PsodA+sodA+sodA, Phag+hag+hag, PtufA+tufA+tufA, PamyE+amyE+amyE, and PfusA+fusA+fusA (Meng F. et al., Enhanced Expression of Pullulanase in *Bacillus subtilis* by New Strong Promoters Mined from Transcriptome Data, both Alone and in Combination, *Microbiol.*, November 2018).

In some embodiments, synthetic, reconstructed promoters may be used with the methods disclosed herein (as in, for example, Liu D. et al., 2018 Construction, Model-Based Analysis, and Characterization of a Promoter Library for Fine-Tuned Gene Expression in *Bacillus subtilis*, *ACS Synth. Biol.* 7, 7, 1785-1797) and others, for example Song Y., et al., 2016 Promoter Screening from *Bacillus subtilis* in Various Conditions Hunting for Synthetic Biology and Industrial Applications, *PLoS ONE* 11(7), Guiziou S., et al., 2016 A Part Toolbox to tune genetic expression in *Bacillus subtilis, Nucleic Acids Res.*, 44(15): 7495-7508.

Ribosomal Binding Sites

In some embodiments, the methods of scarless genomic editing disclosed herein utilize ribosomal binding sites.

Ribosomal binding sites (RBSs) are short sequences of nucleotides that are located upstream of the start codon on an mRNA transcript that is responsible for recruiting ribosomes and initiating translation of protein. Accordingly, they are important regulators of translation and protein expression. However, RBSs can also interact with nearby nucleotides in the 5'UTR, the promoter or coding region of a gene to influence rates of transcription and/or translation. Through these interactions and resulting secondary structure, ribosomal binding sites can "tune" expression of genes.

RBS libraries are common components of synthetic biology toolkits and have been developed for various organisms. In addition, tools have been developed for predicting synthetic RBSs that will interact favorably with a sequence of interest (Salis et al., "Automated design of synthetic ribosome binding sites to control protein expression." *Nat Biotechnol.* 2009; 27:946-950. doi: 10.1038/nbt.1568).

Transcriptional Termination Sequences

In some embodiments, the methods of generating at least one scarless genomic edit disclosed herein utilize termination sequences.

In prokaryotes, two principal mechanisms, termed Rho-independent and Rho-dependent termination, mediate transcriptional termination. Rho-independent termination signals do not require an extrinsic transcription-termination factor, as formation of a stem-loop structure in the RNA transcribed from these sequences along with a series of Uridine (U) residues promotes release of the RNA chain from the transcription complex. Rho-dependent termination, on the other hand, requires a transcription-termination factor called Rho and cis-acting elements on the mRNA. The initial binding site for Rho, the Rho utilization (rut) site, is an extended (~70 nucleotides, sometimes 80-100 nucleotides) single-stranded region characterized by a high cytidine/low guanosine content and relatively little secondary structure in the RNA being synthesized, upstream of the actual terminator sequence. When a polymerase pause site is encountered, termination occurs, and the transcript is released by Rho's helicase activity.

A transcriptional termination sequence may be any nucleotide sequence, which when placed transcriptionally downstream of a nucleotide sequence encoding an open reading frame, causes the end of transcription of the open reading frame. Such sequences are known in the art and may be of prokaryotic, eukaryotic or phage origin. Examples of terminator sequences include, but are not limited to, TgyrA (terminator sequence of *B. subtilis* gyrA gene), TserO_aroC, TcodBA, arginine F gene (argF) terminator, PTH-terminator, pET-T7 terminator, T3-Tφ terminator, pBR322-P4 terminator, vesicular stomatitis virus terminator, rrnB-T1 terminator, rrnC terminator, TTadc transcriptional terminator, and yeast-recognized termination sequences, such as Matα (α-factor) transcription terminator, native α-factor transcription termination sequence, ADR1 transcription termination sequence, ADH2 transcription termination sequence, and GAPD transcription termination sequence. A non-exhaustive listing of transcriptional terminator sequences may be found in the iGEM registry, which is available at: partsregistry.org/Terminators/Catalog.

In some embodiments, transcriptional termination sequences may be polymerase-specific or nonspecific, however, transcriptional terminators selected for use in the present embodiments should form a 'functional combination' with the selected promoter, meaning that the terminator sequence should be capable of terminating transcription by the type of RNA polymerase initiating at the promoter. The identity of the transcriptional termination sequences used may also be selected based on the efficiency with which transcription is terminated from a given promoter. For example, a heterologous transcriptional terminator sequence may be provided transcriptionally downstream of the RNA encoding element to achieve a termination efficiency of at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% from a given promoter.

In some embodiments, the termination sequences are selected from TgyrA, Tsero_aroC, and TcodBA. Where more than one counterselectable marker is used, embodiments disclosed herein provide for each counterselectable marker having a distinct termination sequence.

Transformation of Host Cells

Various methods for transformation are taught herein. In some embodiments, transformation of a competent cell involves heat-shock or electroporation. In some embodiments, transformation is automated. In some embodiments, competent cells are transformed using high-throughput electroporation systems, for example, the VWR®High-throughput Electroporation Systems, BTX™, Bio-Rad® Gene Pulser MXcell™, or other multi-well electroporation systems.

In some embodiments, the vectors of the present disclosure may be introduced into the host cells using any of a variety of techniques, including transformation, transfection, transduction, viral infection, gene guns, or Ti-mediated gene transfer (see Christie, P. J., and Gordon, J. E., 2014 "The *Agrobacterium* Ti Plasmids" Microbiol SPectr. 2014; 2(6); 10.1128). Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., *J. Bacterol.* 153:163-168 (1983); and Becker and Guarente, *Methods in Enzymology* 194:182-187 (1991). In some embodiments, transformed host cells are referred to as recombinant host strains.

In some embodiments, the present disclosure teaches high-throughput transformation of cells using the 96-well plate robotics platform and liquid handling machines of the present disclosure.

In some embodiments, the present disclosure teaches screening transformed cells with one or more selection markers as described above. In one such embodiment, cells transformed with a vector comprising a chloramphenicol resistance marker [Chlor] are plated on media containing effective amounts of the chloramphenicol antibiotic. In other embodiments, cells are transformed with erythromycin and lincomycin [MLS] resistance markers and plated on media containing erythromycin and/or lincomycin. Colony forming units visible on antibiotic-laced media are presumed to have incorporated the vector cassette into their genome. Insertion of the desired sequences can be confirmed via PCR, restriction enzyme analysis, and/or sequencing of the relevant insertion site.

Looping Out of Selected Sequences ("Double Selection")

In some embodiments, the present disclosure teaches methods of counterselection which favor strains having undergone a homologous recombination excising the plasmid backbone to produce a "loop-out" strain. First, clones having integrated the DNA construct by a single crossover are selected for based on the means for positive selection, for example, antibiotic resistance. Clones are allowed to multiply to allow for a second crossover event, looping out the plasmid backbone comprising the selective marker and counterselective marker. When selected clones are then grown on media corresponding to the counterselective marker, for example 4-chloro-$_{DL}$-phenylalanine, only those clones which have lost the counterselective marker ("loop-out" strains) will survive.

Additional looping out methods and techniques are known in the art, and are described in, for example, Tear et al. 2014 "Excision of Unstable Artificial Gene-Specific inverted Repeats Mediates Scar-Free Gene Deletions in *Escherichia coli.*" *Appl. Biochem. Biotech.* 175:1858-1867, and Nakashima et al. 2014 "Bacterial Cellular Engineering by Genome Editing and Gene Silencing." *Int. J. Mol. Sci.* 15(2), 2773-2793.

Screening Loop-Out Strains

In some embodiments, screening of the loop-out strains comprises sequencing, DNA fingerprinting, or phenotypic analysis.

In some embodiments, the present disclosure teaches whole-genome sequencing of the organisms described herein. In other embodiments, the present disclosure also teaches sequencing of plasmids, PCR products, and other oligos as quality controls to the methods of the present disclosure. Sequencing methods for large and small projects are well known to those in the art.

In some embodiments, any high-throughput technique for sequencing nucleic acids can be used in the methods of the disclosure. In some embodiments, the present disclosure teaches ultra deep sequencing of PCR amplicons to identify genetic variations. DNA sequencing techniques include Next-Generation Sequencing (NGS) and classic dideoxy sequencing reactions (Sanger method) using labeled terminators or primers and gel separation in slab or capillary; sequencing by synthesis using reversibly terminated labeled nucleotides, pyrosequencing; 454 sequencing; allele specific hybridization to a library of labeled oligonucleotide probes; sequencing by synthesis using allele specific hybridization to a library of labeled clones that is followed by ligation; real time monitoring of the incorporation of labeled nucleotides during a polymerization step; polony sequencing; and SOLiD sequencing.

In one aspect of the disclosure, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, *Science,* 327: 78-81 (2010)), arrays of wells, which may include bead- or particle-bound templates (such as with 454, e.g. Margulies et al, *Nature,* 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, *Science,* 316: 1481-1414 (2007)).

In another embodiment, the methods of the present disclosure comprise amplifying the isolated molecules either before or after they are spatially isolated on a solid surface. Prior amplification may comprise emulsion-based amplification, such as emulsion PCR, or rolling circle amplification. Also taught is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference.

In another embodiment, screening of the loop-out strains comprises phenotypic analysis. Phenotypic screening is a method used to identify a strain with a specific phenotypic trait and isolate it. Phenotype, as used herein, may apply to any cell property, including molecular phenotypes, such as the level of mRNA for a gene. Phenotypic analysis may comprise, for example, a step-wise process where individual loop-out strains are cultured in media with specific substrates corresponding to the phenotype of interest. Phenotypic assays have become more advanced and sophisticated and allow for high-throughput screening. For example, one skilled in the art may use a semi-automated bacterial phenotypic fingerprint (BPF) in conjunction with machine learning dataset analysis.

In another embodiment, the screening process may comprise a microscopy-based high-throughput screening for alterations in morphological phenotypes. See for example, Zahir, T., Camacho, R., Vitale, R. et al. High-throughput time-resolved morphology screening in bacteria reveals phenotypic responses to antibiotics. *Commun Biol* 2, 269 (2019).

In another embodiment, screening of the loop-out strains may comprise a DNA fingerprint analysis, also referred to as a microbial fingerprint or genetic fingerprint. Methods of DNA fingerprint analysis are well known in the art, and may comprise, for example, a restriction fragment length polymorphism (RFLP), PCR, sequencing, probes, and/or blotting techniques (such as a Southern blot).

In another embodiment, the disclosure relates to microorganisms produced by the methods disclosed herein. In other embodiments, the disclosure relates to *Bacillus* species produced by the methods disclosed herein. In some embodiments, the microorganism or *Bacillus* species produced is subjected to further genetic modification. Such genetic modification techniques may comprise those described herein and/or other techniques well known in the art, including for example, direct gene editing methods using natural or engineered nucleases (ZFNs, TALENS, or CRISPR).

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

Example 1

PheS Confers Sensitivity to Counterselection Agent in B. subtilis

Replicating plasmids bearing PheS(**CO) driving by a range of promoters were constructed using techniques well known in the art.

Figure 1C:
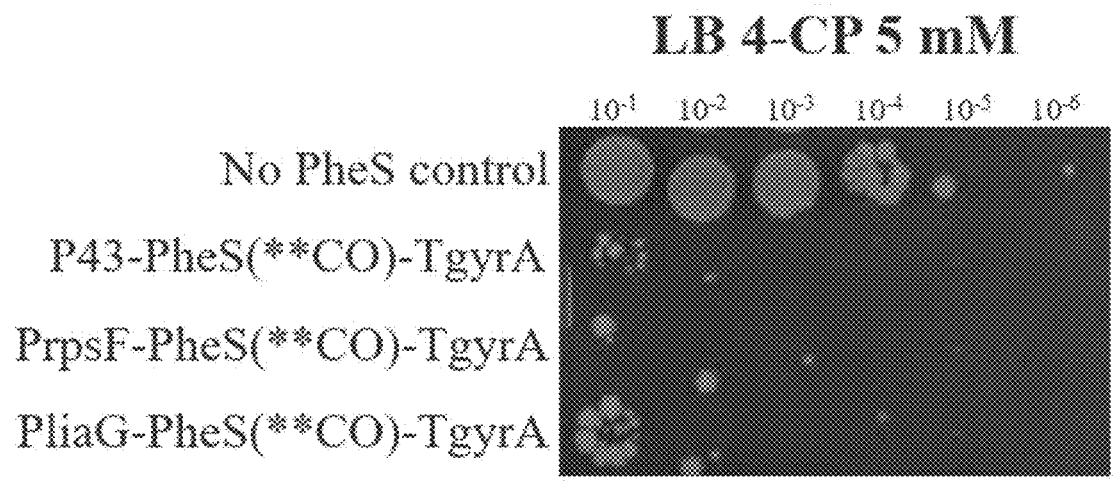
Figure 1D:
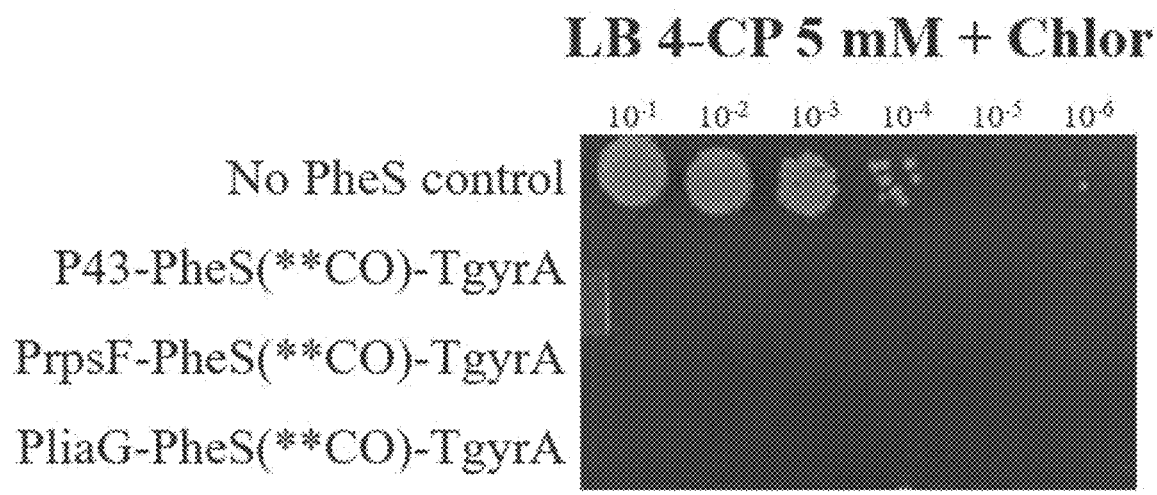

Plasmids were transformed into B. subtilis NRRL #BD-594 (S30A) strain and tested for sensitivity. As shown in FIG. 1A-1D, a culture dilution series were spotted in six replicates onto LB media (FIG. 1A), LB media with the selective antibiotic chloramphenicol [Chlor] (FIG. 1B), LB media with the counterselection reagent 4CP (FIG. 1C), or the combination of both chloramphenicol and 4CP (FIG. 1D), and incubated for one day. S30A strains with PheS constructs were unaffected on selective media, but are significantly inhibited on 4CP (FIG. 1C). When both chloramphenicol and 4CP were included in the media there was complete cell death, as the plasmid could not be looped out due to the presence of chloramphenicol (FIG. 1D). These results indicate that PheS(**CO) can serve as a counterselection marker in B. subtilis.

Example 2

PheS Confers Sensitivity to Counterselection Agent in B. subtilis Strain 168

Figure 2A:
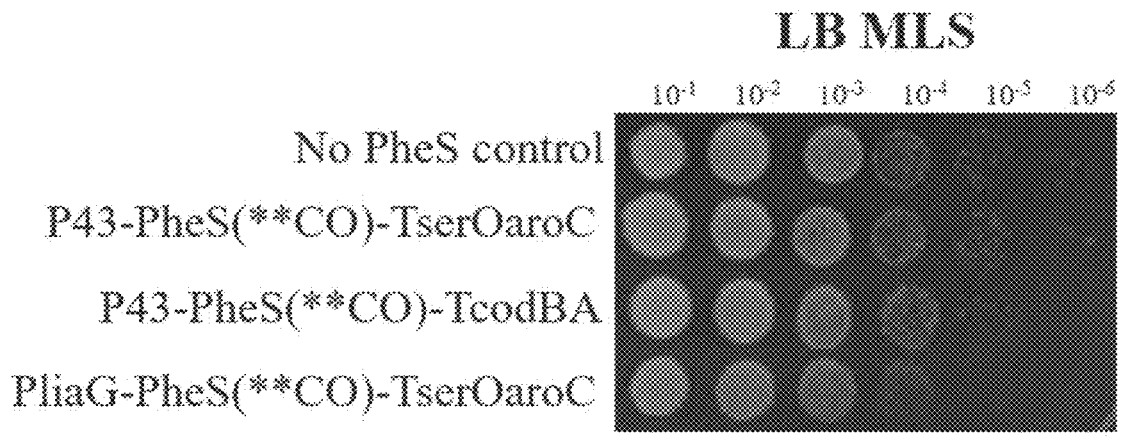
FIG. 2A and FIG. 2B show photographs of a culture dilution series of *B. subtilis* strain 168 transformed with plasmids bearing PheS(**CO) driven by different promoters. Cultures were plated on LB plates having selective antibiotic (Erythromycin and Lincomycin [MLS]) (FIG. 2A), or MLS+counterselection reagent 4CP (FIG. 2B).
Figure 2B:
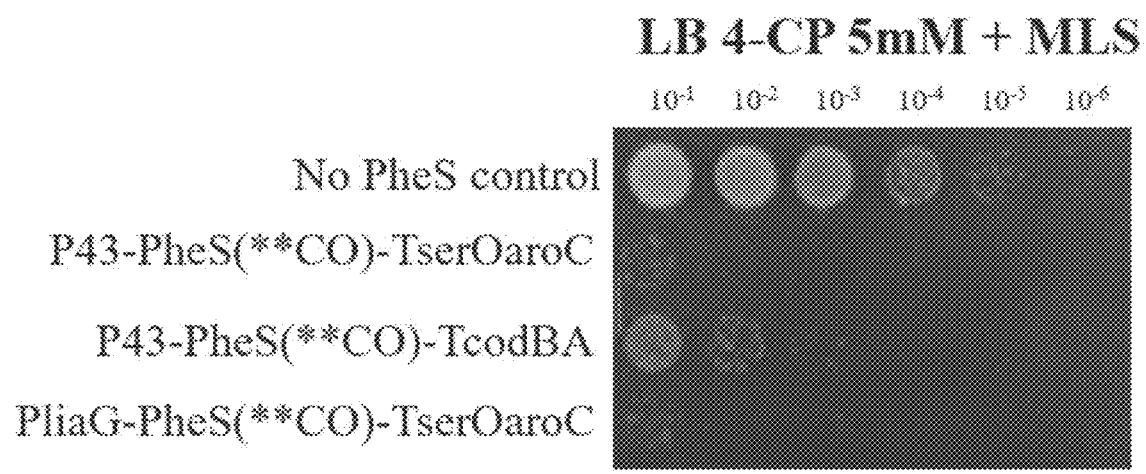

Replicating plasmids bearing PheS(CO) driving by a range of promoters and having different termination sequences were constructed as described above and transformed into B. subtilis 168 (BS168) strain and tested for sensitivity. As shown in FIGS. 2A and 2B, a culture dilution series were spotted in six replicates onto LB media with either the selective antibiotic (Erythromycin and Lincomycin [MLS]) (FIG. 2A), or MLS+ the counterselection reagent 4CP (FIG. 2B), and incubated for one day. BS168 strains with PheS constructs were unaffected on selective media, but were significantly inhibited on 4CP+MLS, where the strain is forced to maintain the plasmid. These results indicate that PheS(CO) can serve as a counterselection marker in B. subtilis in multiple genetic backgrounds.

Example 3

PheS Confers Sensitivity to Counterselection Agent in B. licheniformis Strain DSM13

Figure 3A:
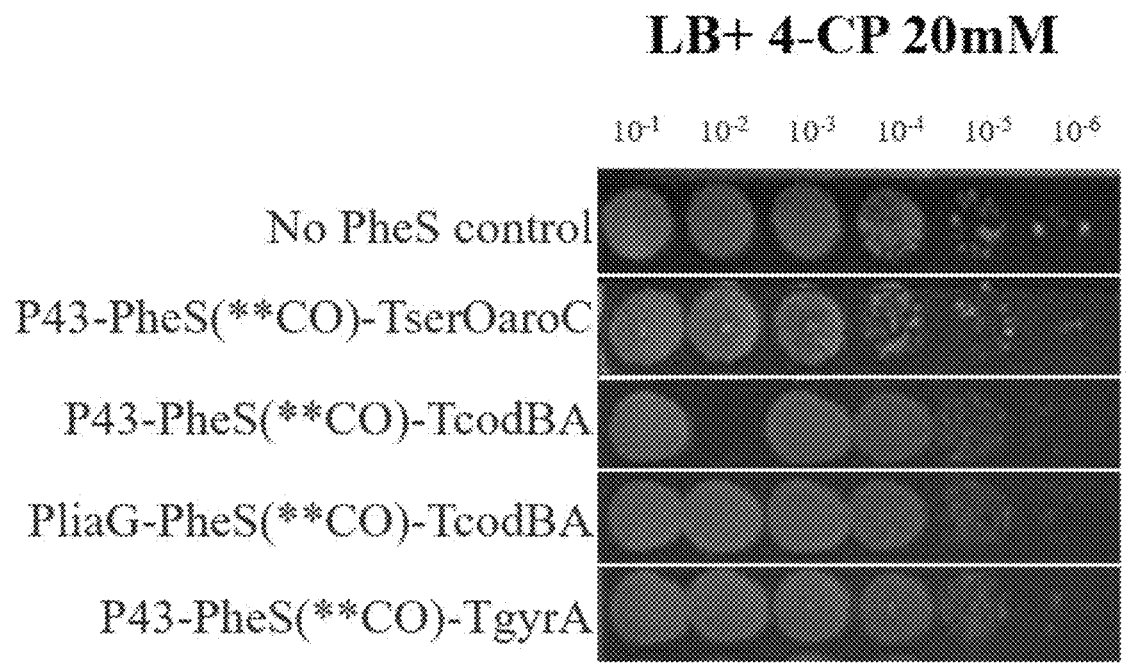
FIG. 3A and FIG. 3B show photographs of a culture dilution series of *B. licheniformis* strain DSM13 transformed with plasmids bearing PheS(**CO) driven by different promoters. Cultures were plated on LB plates having counterselection reagent 4CP (FIG. 3A) or selective antibiotic MLS+4CP (FIG. 3B).
Figure 3B:
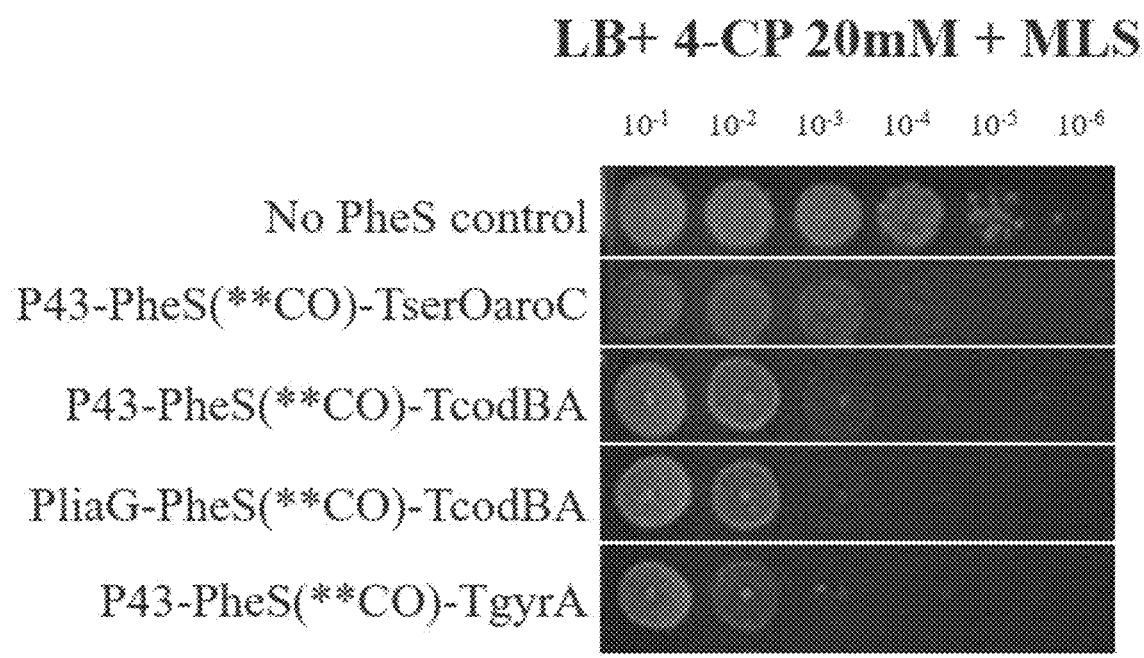

Replicating plasmids bearing PheS(CO) driving by a range of promoters and having different termination sequences were constructed as described above and transformed into B. licheniformis DSM13 strain and tested for sensitivity. As shown in FIGS. 3A and 3B, culture dilution series were spotted in six replicates onto LB media with either the counterselection reagent 4CP (FIG. 3A) or 4CP+ selective antibiotic MLS (FIG. 3B), and incubated for one day. All strains were unaffected on 4CP without positive selection (FIG. 3A). The strains containing PheS(CO) were significantly inhibited on 4CP with MLS selection in comparison to the control strain (lacking counterselectable marker PheS), as the plasmid cannot be lost due to the presence of MLS (FIG. 3B). These results indicate that PheS(**CO) can serve as a counterselection marker in B. licheniformis.

Example 4

Loop-Out to Edit Rates with and without Phes Counterselection in B. Subtilis Strain S30A To investigate loop-out to edit rates, B. subtilis strain S30 was transformed with PheS(**CO) under the control of P43, PliaG, PrpsF, or Pspac promoters and edit rates of two different loci, spoIIE and cotS were analyzed. All constructs contained the terminator sequence of the B. subtilis DNA gyrase subunit A gene (TgyrA) to minimize transcriptional read-through, and all constructs contained a positive selection marker. Colonies were plated on LB plus Chloramphenicol to select for positive transformants, which were subsequently grown on media comprising 10 mM 4-CP to select for loop-out strains. Colonies were screened by NGS sequencing.

As shown below in Table 1, loop-out rates to correct edit for PheS(**CO) containing strains can reach upwards of (but not limited to) 89% as compared to 2.5% for the markerless control.

TABLE 1

Loop-out to edit rates in B. subtilis S30A with PheS(**CO) counterselectable marker

| Counterselectable Marker | Loop-out to Edit | Loci | Number of Colonies Tested |
|---|---|---|---|
| Markerless | 2.5% | spoIIE | 570 |
| P43-PheS(**CO)-TgyrA | 89% | spoIIE | 22 |
| PliaG-PheS(**CO)-TgyrA | 36% | spoIIE | 39 |
| PliaG-PheS(**CO)-TgyrA | 46% | cotS | 34 |
| PrpsF-PheS(**CO)-TgyrA | 69% | cotS | 26 |
| Pspac-PheS(**CO)-TgyrA | 30% | cotS | 48 |

Example 5

Figure 4A:
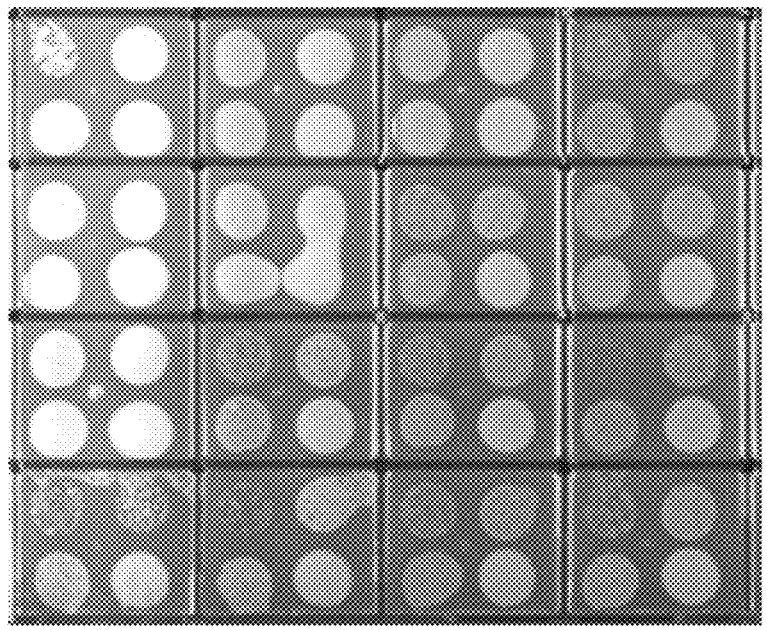
FIG. 4A and FIG. 4B show photographs of a culture dilution series of B. subtilis strain S30A without PheS (CO) (FIG. 4A) or transformed with plasmids bearing PheS(CO) driven by the PliaG promoter (FIG. 4B). Cultures were plated on media having counterselection reagent 4CP.
Figure 4B:
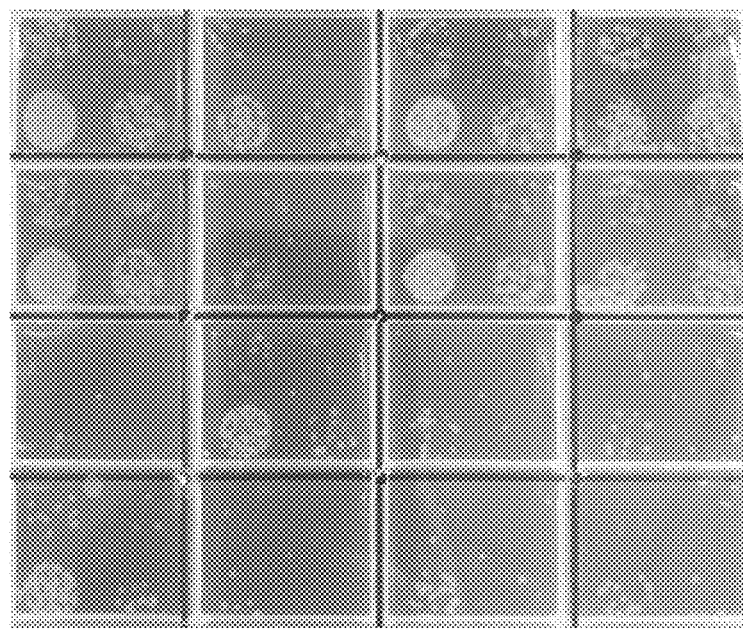

Loop-Out to Edit Rates with and without PheS Counterselection in HTP Builds of B. subtilis Strain S30A High throughput builds were attempted in B. subtilis strain S30A with constructs that were identical besides the counterselection cassette; one did not express PheS (FIG. 4A) while the other comprised PheS(CO) driven by the PliaG promoter (FIG. 4B). The integrated strains were then serially diluted onto media having the counterselection reagent 4CP. As shown in FIG. 4A, the markerless construct grows a lawn at all dilutions, indicating loop-out is not occurring. However, constructs with PheS(CO) grow at a much lower density and successfully undergo loop-out. As indicated in Table 2 below, the overall build success rate for the markerless edits was 0%, while the build success rate for the constructs bearing PheS(**CO) was 86.3%.

TABLE 2

Loop-out rates for high throughput builds in *B. subtilis* strain S30A

| Counterselectable Marker | Build Success Rate | Number of Strains Attempted |
|---|---|---|
| Markerless | 0% | 86 |
| PliaG-PheS(**CO)-TgyrA | 86.3% | 159 |

Example 6

Loop-Out Edit Rates with and without PheS Counterselection in *B. licheniformis* Strain DSM13

To investigate loop-out to edit rates in *B. licheniformis*, strain DSM13 was transformed with PheS(CO) under the control of P43 or PliaG promoters and edit rates of ZBL30595 were analyzed. All constructs contained a terminator sequence of TserO_aroC or TcodBA to minimize transcriptional read-through. As shown below in Table 3, loop-out rates to correct edit for PheS(CO) containing strains can reach upwards of (but not limited to) 11.9% as compared to 0.8% for the markerless control.

TABLE 3

Loop-out to edit rates in *B. licheniformis* DSM13 with PheS(**CO) counterselectable marker

| Counterselectable Marker | Loop-out to Edit | Loci | Number of Colonies Tested |
|---|---|---|---|
| Markerless | 0.8% | ZBL30595 | 378 |
| P43-PheS(**CO)-TserO_aroC | 8.2% | ZBL30595 | 196 |
| P43-PheS(**CO)-TcodBA | 9.8% | ZBL30595 | 255 |
| PliaG-PheS(**CO)-TcodBA | 11.9% | ZBL30595 | 126 |

Example 7

Expressing Two Copies of a Counterselectable Marker Decreases Breakage in *B. subtilis*

In addition to PheS(CO), a second codon optimized version of the counterselectable marker, PheS() was generated as described herein, having an identical amino acid sequence. As shown in FIG. 5, an alignment of SEQ ID NO: 1 (PheS(CO)) and SEQ ID NO: 2 (PheS()) using EMBL-EBI, (EMBOSS Water, Smith-Waterman algorithm) indicates approximately 75% shared identity, with a maximum tandem length of 14 base pairs to prevent homologous recombination between the two sequences. However as will be understood by one skilled in the art, homologous recombination can be reduced or disrupted by even a single base pair difference (Koren, P. et al., (2000), Influence of homology size and polymorphism on plasmid integration in the yeast CYC1 DNA region. *Current Genetics*. 37. 292-297).

Figure 6A:
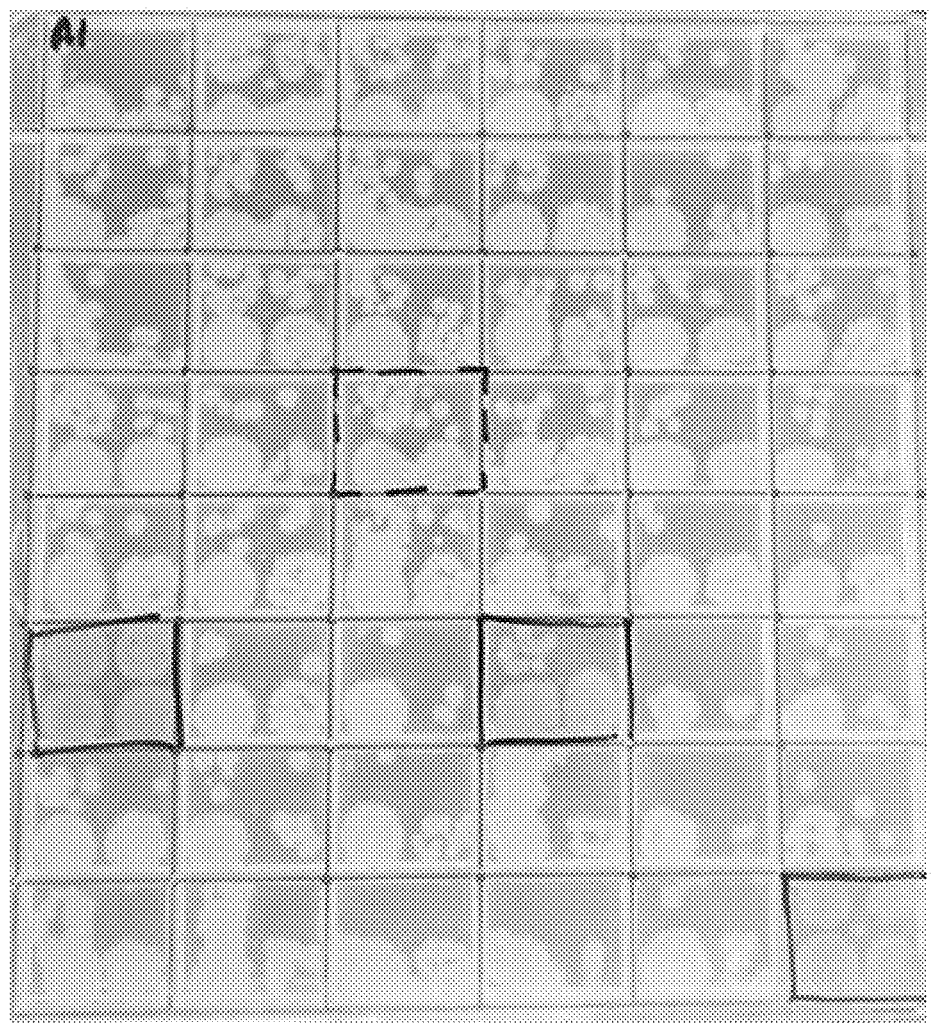
FIG. 6A and FIG. 6B show photographs of a culture dilution series of *B. subtilis* strain 530A transformed with one copy of PheS(CO) driven by PliaG promoter and having a TgyrA termination sequence (FIG. 6A) and the other having two counterselectable markers, PheS(CO) and PheS(**) driven by PliaG and TgyrA promoters, respectively, with TgryA and TserOaroC termination sequences, respectively (FIG. 6B). Cultures were plated on media having counterselection reagent 4CP.
Figure 6B:
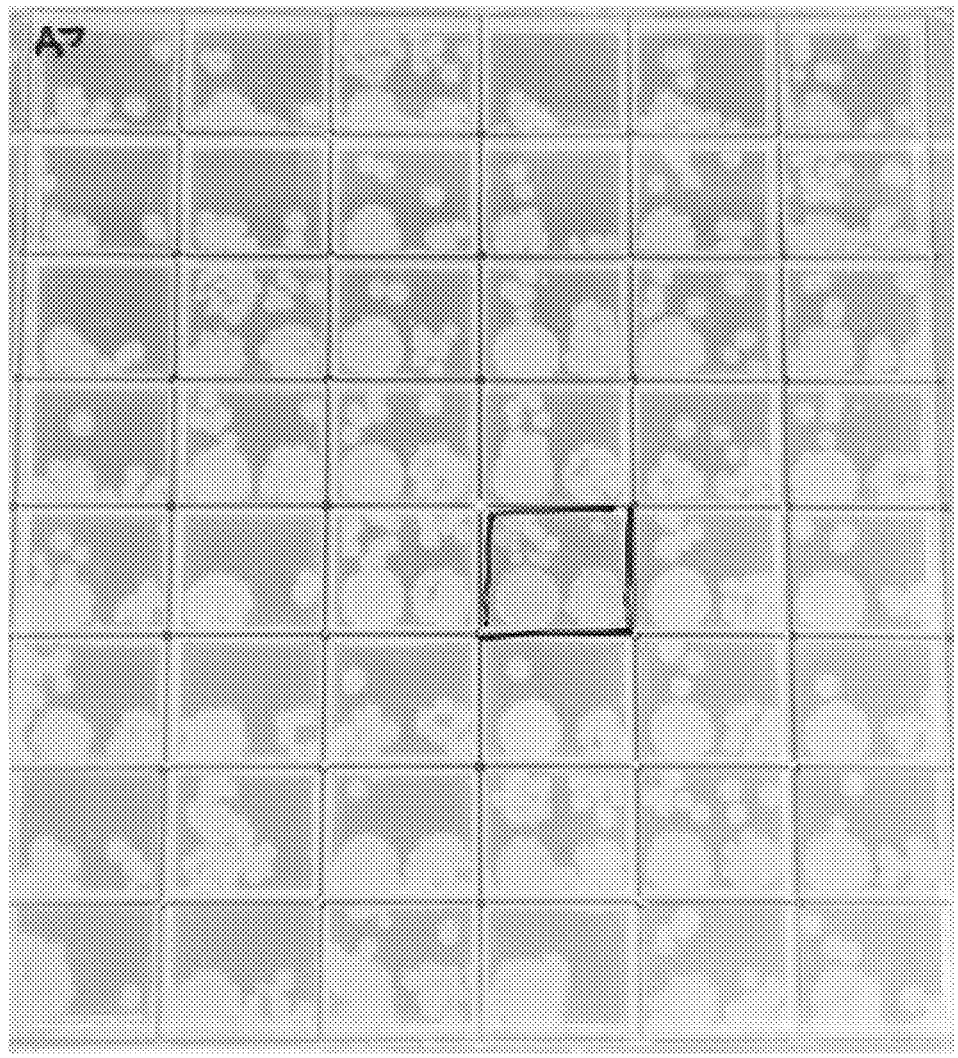

The 1×PheS(CO) construct (FIG. 6A) was driven by PliaG promoter and had a termination sequence of TgryA. The 2× construct comprising PheS(CO) and PheS(**) was driven by PliaG and PrpsF promoters, respectively, with TgyrA and TserOaroC termination sequences, respectively (FIG. 6B). Constructs were transformed into *B. subtilis* S30A and then spot plated with serial dilutions onto LB with 5 mM 4CP. For constructs with one copy of PheS(CO) breakage occurred at an 8% rate (4/48), (FIG. 6A, denoted with black squares), however the construct comprising PheS (CO) and PheS(**) breakage was lowered to 2% (1/48), (FIG. 6B, denoted with a black square), demonstrating that expression two copies of a counterselectable marker in tandem having distinct nucleotide sequences decreases spontaneous breakage of counterselection, thereby reducing false positives and increasing the effectiveness of counterselection.

Brief Description of the Sequence Listings

SEQ ID NO: 1 shows the nucleic acid sequence of the codon optimized PheS(**CO) counterselection marker.

SEQ ID NO: 2 shows the nucleic acid sequence of the independently codon optimized PheS(**) counterselection marker.

SEQ ID NO: 3 shows the corresponding amino acid sequence of SEQ ID NO: 1 and SEQ ID NO: 2.

Additional Embodiments of the Disclosure

Other subject matter contemplated by the present disclosure is set out in the following numbered embodiments:

1. A high-throughput (HTP) method for generating at least one scarless genomic edit in a *Bacillus* species, comprising:
providing a plasmid or linear DNA construct comprising a sequence of interest, a means for positive selection, and a counterselectable marker, wherein the counterselectable marker is an α-subunit of Phenylalanyl-tRNA ligase, (PheS) that has been codon optimized for *Bacillus* and further comprises A309G/T255S mutations, and wherein the counterselectable marker is operably linked to at least one promoter;
transforming a *Bacillus* species with the DNA construct;
selecting for a *Bacillus* strain having integrated the DNA construct based on the means for positive selection;
growing the *Bacillus* strain having integrated the DNA construct in the presence of 4-chlorphenylalanine to select for a *Bacillus* strain having undergone a homologous recombination event excising the backbone of the plasmid containing the counterselectable marker to produce a loop-out strain; and
screening the loop-out strain for the presence of the sequence of interest to produce a modified *Bacillus* strain having at least one scarless genomic edit.

2. The method of embodiment 1, wherein the PheS that has been codon optimized comprises SEQ ID NO: 1 (herein after referred to as PheS(**CO)), a sequence at least 90% identical thereto.

3. The method of embodiments 1 or 2, wherein the at least one promoter operably linked to the counterselectable marker is constitutive, inducible, differentially inducible, endogenous, heterologous, synthetic, a dual promoter, or a tandem promoter cluster.

4. The method of any one of embodiments 1-3, wherein the at least one promoter is selected from the group consisting of PliaG, P43, PilaI, PrpsF, Pspac, and Pspank.

5. The method of any one of embodiments 1-4, wherein the at least one promoter is a dual promoter or tandem promoter selected from the group consisting of PHpaII-PamyQ' and PgsiB-PHpaII.

6. The method of any one of embodiments 1-5, wherein the DNA construct further comprises a ribosomal binding site.

7. The method of any one of embodiments 1-6, wherein the DNA construct further comprises a termination sequence.

8. The method of embodiment 7, wherein the termination sequence is selected from the group consisting of TgyrA, Tsero_aroC, and TcodBA.

9. The method of any one of embodiments 1-8, wherein the *Bacillus* species is transformed with the construct using natural competence, conjugation, electroporation, transduction, or protoplast transformation.

10. The method of any one of embodiments 1-9, wherein the strain having integrated the DNA construct is grown on or in media containing between 1 mM and 20 mM 4-chlorphenylalanine.

11. The method of any one of embodiments 1-10, wherein screening of the loop-out strain comprises sequencing, DNA fingerprinting, or phenotypic analysis.

12. The method of any one of embodiments 1-11, wherein the sequence of interest is an endogenous gene having a least one mutation sequence.

13. The method of embodiment 12, wherein the mutation sequence comprises a mutation selected from the group consisting of:
 a. a single nucleotide insertion;
 b. an insertion of two or more nucleotides;
 c. an insertion of a nucleic acid sequence encoding one or more proteins;
 d. a single nucleotide deletion;
 e. a deletion of two or more nucleotides;
 f. a deletion of one or more coding sequences;
 g. a substitution of a single nucleotide;
 h. a substitution of two or more nucleotides;
 i. two or more non-contiguous insertions, deletions, and/or substitutions; and
 j. any combination thereof.

14. The method of any one of embodiments 1-13, wherein the sequence of interest is a heterologous gene.

15. A genetically modified *Bacillus* strain produced by any one of the methods of embodiments 1-14.

16. The genetically modified *Bacillus* strain of embodiment 15, wherein the *Bacillus* species is selected from the group consisting of *B. coagulans, B. ginsengihumi, B. shackletonii, B. aerius, B. aerophilus, B. stratosphericus, B. licheniformis, B. sonorensis, B. amyloliquefaciens, B. velezensis, B. atrophaeus, B. pumilus, B. safensis, B. altitudinis, B. vallismortis, B. subtilis, B. tequilensis, B. mojavensis, B. carboniphilus, B. oleronius, B. sporothermodurans, B. acidicola, B. aquimaris, B. vietnamensis, B. marisflavi, B. seohaeanensis, B. endophyticus,* and *B. humi*.

17. The modified *Bacillus* strain of embodiment 16, wherein the modified *Bacillus* strain is subjected to further genetic modification.

18. A DNA construct comprising the counterselection marker PheS(**CO) comprising SEQ ID NO: 1, or a sequence at least 90% identical thereto.

19. A *Bacillus* strain having the DNA construct of embodiment 18.

20. The method of embodiment 1, wherein the PheS that has been codon optimized comprises SEQ ID NO: 2 (hereinafter referred to as PheS(**)), or a sequence at least 75% identical thereto.

21. The method of embodiment 20, wherein the at least one promoter operably linked to the counterselectable marker is constitutive, inducible, differentially inducible, endogenous, heterologous, synthetic, a dual promoter, or a tandem promoter cluster.

22. The method of any one of embodiments 20-21, wherein the at least one promoter is selected from the group consisting of PliaG, P43, PilaI, PrpsF, Pspac, and Pspank.

23. The method of any one of embodiments 20-22, wherein the promoter is a dual promoter or tandem promoter selected from the group consisting of PHpaII-PamyQ' and PgsiB-PHpaII.

24. The method of any one of embodiments 20-23, wherein the DNA construct further comprises a ribosomal binding site.

25. The method of any one of embodiments 20-24, wherein the DNA construct further comprises a termination sequence.

26. The method of embodiment 25, wherein the termination sequence is selected from the group consisting of TgyrA, Tsero_aroC, and TcodBA.

27. The method of any one of embodiments 20-26, wherein the *Bacillus* species is transformed with the construct using natural competence, conjugation, electroporation, transduction, or protoplast transformation.

28. The method of any one of embodiments 20-27, wherein the strain having integrated the DNA construct is grown on or in media containing between 1 mM and 20 mM 4-chlorphenyl alanine.

29. The method of any one of embodiments 20-28, wherein the screening of the loop-out strain comprises sequencing, DNA fingerprinting, or phenotypic analysis.

30. The method of any one of embodiments 20-29, wherein the sequence of interest is an endogenous gene having a least one mutation sequence.

31. The method of embodiment 30, wherein the mutation sequence comprises a mutation selected from the group consisting of:
 a. a single nucleotide insertion;
 b. an insertion of two or more nucleotides;
 c. an insertion of a nucleic acid sequence encoding one or more proteins;
 d. a single nucleotide deletion;
 e. a deletion of two or more nucleotides;
 f. a deletion of one or more coding sequences;
 g. a substitution of a single nucleotide;
 h. a substitution of two or more nucleotides;
 i. two or more non-contiguous insertions, deletions, and/or substitutions; and
 j. any combination thereof.

32. The method of any one of embodiments 20-29, wherein the sequence of interest is a heterologous gene.

33. A genetically modified *Bacillus* strain produced by any one of the methods of embodiments 20-33.

34. The genetically modified *Bacillus* strain of embodiment 33, wherein the *Bacillus* species is selected from the group consisting of *B. coagulans, B. ginsengihumi, B. shackletonii, B. aerius, B. aerophilus, B. stratosphericus, B. licheniformis, B. sonorensis, B. amyloliquefaciens, B. velezensis, B. atrophaeus, B. pumilus, B. safensis, B. altitudinis, B. vallismortis, B. subtilis, B. tequilensis, B. mojavensis, B. carboniphilus, B. oleronius, B. sporothermodurans, B. acidicola, B. aquimaris, B. vietnamensis, B. marisflavi, B. seohaeanensis, B. endophyticus,* and *B. humi*.

35. The modified *Bacillus* strain of embodiment 34, wherein the modified *Bacillus* strain is subjected to further genetic modification.

36. A DNA construct comprising the counterselection marker PheS(**) comprising SEQ ID NO: 2, or a sequence at least 75% identical thereto.

37. A *Bacillus* strain having the DNA construct of embodiment 36.

38. A method for generating at least one scarless genomic edit in a *Bacillus* species, comprising:

providing a plasmid or linear DNA construct comprising a sequence of interest, a means for positive selection, and two counterselectable markers, wherein the counterselectable markers are an α-subunit of phenylalanyl-tRNA ligase, (PheS) that have been codon optimized for *Bacillus* and further comprise A309G/T255S mutations, wherein the counterselectable markers have a maximum tandem identity length of 500 base pairs when aligned with each other, and wherein each counterselectable marker is operably linked to at least one promoter;

transforming a *Bacillus* species with the DNA construct;

selecting for a *Bacillus* strain having integrated the DNA construct based on the means for positive selection;

growing the *Bacillus* strain having integrated the DNA construct in the presence of 4-chlorphenylalanine to select for a *Bacillus* strain having undergone a homologous recombination event excising the backbone of the plasmid containing the counterselectable marker to produce a loop-out strain; and screening the loop-out strain for the presence of the sequence of interest to produce a modified *Bacillus* strain having at least one scarless genomic edit.

39. The method of embodiment 38, wherein one counterselectable marker comprises SEQ ID NO: 1, or a sequence at least 90% identical thereto, and the other comprises SEQ ID NO: 2, or a sequence at least 75% identical thereto.

40. The method of embodiments 38 or 39, wherein the at least one promoter operably linked to each counterselectable marker is constitutive, inducible, differentially inducible, endogenous, heterologous, synthetic, a dual promoter, or a tandem promoter cluster.

41. The method of any one of embodiments 38-40, wherein the at least one promoter is selected from the group consisting of PliaG, P43, PliaI, PrpsF, Pspac, and Pspank.

42. The method of any one of embodiments 38-41, wherein the at least one promoter is a dual promoter or tandem promoter selected from the group consisting of PHpaII-PamyQ' and PgsiB-PHpaII.

43. The method of any one of embodiments 38-42, wherein each counterselectable marker has a distinct operably linked promoter.

44. The method of any one of embodiments 38-43, wherein the DNA construct further comprises a ribosomal binding site.

45. The method of any one of embodiments 38-44, wherein each of the counterselectable markers further comprises a termination sequence.

46. The method of embodiment 45, wherein the termination sequence is selected from the group consisting of TgyrA, Tsero_aroC, and TcodBA.

47. The method of embodiment 45 or 46, wherein each counterselectable marker has a distinct termination sequence.

48. The method of any one of embodiments 38-47, wherein the *Bacillus* species is transformed with the construct using natural competence, conjugation, electroporation, transduction, or protoplast transformation.

49. The method of any one of embodiments 38-48, wherein the strain having integrated the DNA construct is grown on or in media containing between 1 mM and 20 mM 4-chlorphenyl alanine.

50. The method of any one of embodiments 38-49, wherein screening of the loop-out strain comprises sequencing, DNA fingerprinting, or phenotypic analysis.

51. The method of any one of embodiments 38-50, wherein the sequence of interest is an endogenous gene having a least one mutation sequence.

52. The method of embodiment 51, wherein the mutation sequence comprises a mutation selected from the group consisting of:

a. a single nucleotide insertion;
b. an insertion of two or more nucleotides;
c. an insertion of a nucleic acid sequence encoding one or more proteins;
d. a single nucleotide deletion;
e. a deletion of two or more nucleotides;
f. a deletion of one or more coding sequences;
g. a substitution of a single nucleotide;
h. a substitution of two or more nucleotides;
i. two or more non-contiguous insertions, deletions, and/or substitutions; and
j. any combination thereof.

53. The method of any one of embodiments 38-52, wherein the sequence of interest is a heterologous gene.

54. A genetically modified *Bacillus* strain produced by any one of the methods of embodiments 38-53.

55. The genetically modified *Bacillus* strain of embodiment 54, wherein the *Bacillus* species is selected from the group consisting of *B. coagulans, B. ginsengihumi, B. shackletonii, B. aerius, B. aerophilus, B. stratosphericus, B. licheniformis, B. sonorensis, B. amyloliquefaciens, B. velezensis, B. atrophaeus, B. pumilus, B. safensis, B. altitudinis, B. vallismortis, B. subtilis, B. tequilensis, B. mojavensis, B. carboniphilus, B. oleronius, B. sporothermodurans, B. acidicola, B. aquimaris, B. vietnamensis, B. marisflavi, B. seohaeanensis, B. endophyticus,* and *B. humi.*

56. The modified *Bacillus* strain of embodiment 55, wherein the modified *Bacillus* strain is subjected to further genetic modification.

57. A DNA construct comprising the counterselection marker PheS(CO) comprising SEQ ID NO: 1, or a sequence at least 90% identical thereto, and the counterselection marker PheS() comprising SEQ ID NO: 2, or a sequence at least 75% identical thereto.

58. A *Bacillus* strain having the DNA construct of embodiment 57.

59. A high-throughput (HTP) method for generating at least one scarless genomic edit in a microorganism, comprising:

providing a plasmid or linear DNA construct comprising a sequence of interest and at least one counterselectable marker, wherein the at least one counterselectable marker is a homolog of the α-subunit of Phenylalanyl-tRNA ligase, (PheS) that has been codon optimized for a microorganism, and further comprises homologous mutations corresponding to A309G/T255S of *Bacillus* PheS, and wherein the at least one counterselectable marker is operably linked to at least one promoter;

transforming the microorganism with the DNA construct to produce a transformed strain;

growing the transformed strain in the presence of 4-chlorphenylalanine to select for a strain having undergone a recombination event excising the backbone of the plasmid containing the at least one counterselectable marker to produce a loop-out strain; and screening the loop-out strain for the presence of the sequence of interest to produce a scarless genetically modified microorganism.

60. The method of embodiment 59, wherein the DNA construct comprises two counterselectable markers, wherein the markers have been independently codon optimized for the microorganism and are sufficiently distinct to prevent homologous recombination between the two markers.

61. The method of embodiment 60, wherein the two counterselectable markers have a maximum tandem identity length of 500 base pairs when aligned with each other.

62. The method of embodiment 60, wherein the two counterselectable markers have a maximum tandem identity length of 250 base pairs when aligned with each other.

63. The method of embodiment 60, wherein the two counterselectable markers have a maximum tandem identity length of 100 base pairs when aligned with each other.

64. The method of embodiment 60, wherein the two counterselectable markers have a maximum tandem identity length of 25 base pairs when aligned with each other.

65. The method of any one of embodiments 59-64, wherein the DNA construct further comprises a means for positive selection.

66. The method of any one of embodiments 59-65, wherein the DNA construct further comprises a ribosomal binding site.

67. The method of any one of embodiments 59-66, wherein the at least one counterselectable marker further comprises a termination sequence.

68. The method of any one of embodiments 59-67, wherein the sequence of interest is an endogenous gene having a least one mutation sequence.

69. The method of embodiment 68, wherein the mutation sequence comprises a mutation selected from the group consisting of:
  a. a single nucleotide insertion;
  b. an insertion of two or more nucleotides;
  c. an insertion of a nucleic acid sequence encoding one or more proteins;
  d. a single nucleotide deletion;
  e. a deletion of two or more nucleotides;
  f. a deletion of one or more coding sequences;
  g. a substitution of a single nucleotide;
  h. a substitution of two or more nucleotides;
  i. two or more non-contiguous insertions, deletions, and/or substitutions; and
  j. any combination thereof.

70. The method of any one of embodiments 59-67, wherein the sequence of interest is a heterologous gene.

71. A microorganism produced by the method of any one of embodiments 59-70.

72. The method of embodiment 71, wherein the microorganism is a *Bacillus* species.

73. The method of embodiment 72, wherein the sequence of interest is a DNA fragment having homology to a genomic locus of the *Bacillus* species.

74. The method of any one of embodiments 59-73, wherein the screening the loop-out strain comprises sequencing, DNA fingerprinting, or phenotypic analysis.

75. The method of any one of embodiments 59-74, wherein the method results in greater than 2.5% of microorganisms containing a scarless genetic modification.

76. A high-throughput (HTP) method for generating at least one scarless genomic edit in a microorganism, comprising:
  providing a plasmid or linear DNA construct comprising a sequence of interest, a means for positive selection, and two counterselectable markers, wherein each of the counterselectable markers have been independently codon optimized for the microorganism and have a maximum tandem identity length of 500 base pairs when aligned with each other, and wherein each counterselectable marker is operably linked to at least one promoter;
  transforming the microorganism with the DNA construct;
  selecting for a microorganism strain having integrated the DNA construct based on the means for positive selection;
  selecting for a microorganism having undergone a homologous recombination event excising the backbone of the plasmid containing the counterselectable markers to produce a loop-out strain; and
  screening the loop-out strain for the presence of the sequence of interest to produce a modified microorganism having at least one scarless genomic edit.

77. The method of embodiment 76, wherein the microorganism is a *Bacillus* species.

78. The method of embodiment 77, wherein the counterselectable markers are an α-subunit of phenylalanyl-tRNA ligase, (PheS) and further comprise A309G/T255S mutations.

79. The method of embodiment 78, wherein one counterselectable marker comprises SEQ ID NO: 1, or a sequence at least 90% identical thereto, and the other comprises SEQ ID NO: 2, or a sequence at least 75% identical thereto.

80. The method of any one of embodiments 76-79, wherein the at least one promoter operably linked to each counterselectable marker is constitutive, inducible, differentially inducible, endogenous, heterologous, synthetic, a dual promoter, or a tandem promoter cluster.

81. The method of any one of embodiments 76-80, wherein the at least one promoter is selected from the group consisting of PliaG, P43, PilaI, PrpsF, Pspac, and Pspank.

82. The method of any one of embodiments 76-81, wherein each counterselectable marker has a distinct operably linked promoter.

83. The method of any one of embodiments 76-82, wherein each of the counterselectable markers further comprises a termination sequence.

84. The method of embodiment 83, wherein the termination sequence is selected from the group consisting of TgyrA, Tsero_aroC, and TcodBA.

85. The method of embodiment 83 or 84, wherein each counterselectable marker has a distinct termination sequence.

86. The method of any one of embodiments 78-85, wherein the strain having integrated the DNA construct is grown on or in media containing between 1 mM and 20 mM 4-chlorphenyl alanine.

87. The method of any one of embodiments 76-86, wherein screening of the loop-out strain comprises sequencing, DNA fingerprinting, or phenotypic analysis.

88. The method of any one of embodiments 76-87, wherein the sequence of interest is an endogenous gene or a heterologous gene, wherein the endogenous gene has at least one mutation sequence selected from the group consisting of:
  a. a single nucleotide insertion;
  b. an insertion of two or more nucleotides;
  c. an insertion of a nucleic acid sequence encoding one or more proteins;
  d. a single nucleotide deletion;
  e. a deletion of two or more nucleotides;
  f. a deletion of one or more coding sequences;
  g. a substitution of a single nucleotide;
  h. a substitution of two or more nucleotides;
  i. two or more non-contiguous insertions, deletions, and/or substitutions; and
  j. any combination thereof.

89. A genetically modified *Bacillus* strain produced by the method of any one of embodiments 77-88.

90. The modified *Bacillus* strain of claim 89, wherein the modified *Bacillus* strain is subjected to further genetic modification.

91. A genetically modified microorganism produced by the method of any one of embodiments 76-90.

92. An isolated nucleic acid comprising SEQ ID NO: 1, or a sequence at least 90% identical thereto.

93. An isolated nucleic acid comprising SEQ ID NO: 2, or a sequence at least 75% identical thereto.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, PCT/US2016/065465 (WO 2017/100377 A1), filed Dec. 7, 2016, and entitled: Microbial Strain Improvement By A HTP Genomic Engineering Platform is hereby incorporated by reference.

What is claimed is:

1. An isolated nucleic acid comprising SEQ ID NO: 1, or a sequence at least 90% identical thereto, or SEQ ID NO: 2, or a sequence at least 75% identical thereto.

2. A DNA construct comprising at least one of the isolated nucleic acids of claim 1.

3. The DNA construct of claim 2, wherein the construct comprises a sequence of interest and a positive selectable marker.

4. The DNA construct of claim 2, wherein the construct comprises one of:
   (i) SEQ ID NO: 1, or a sequence at least 90% identical thereto;
   (ii) SEQ ID NO: 2, or a sequence at least 75% identical thereto; or
   (iii) SEQ ID NO:1, or a sequence at least 90% identical thereto, and SEQ ID NO: 2, or a sequence at least 75% identical thereto.

5. The DNA construct of claim 4, wherein each of the sequences in (i), (ii), or (iii) is operably linked to at least one promoter.

6. The DNA construct of claim 5, wherein the at least one promoter operably linked to each sequence is constitutive, inducible, differentially inducible, endogenous, heterologous, synthetic, a dual promoter, or a tandem promoter cluster.

7. The DNA construct of claim 6, wherein the at least one promoter is selected from the group consisting of PliaG, P43, PilaI, PrpsF, Pspac, and Pspank.

8. The DNA construct of claim 5, wherein each of the sequences in (iii) has a distinct operably linked promoter.

9. The DNA construct of claim 4, wherein each of the sequences in (i), (ii), or (iii) further comprises a termination sequence.

10. The DNA construct of claim 9, wherein the termination sequence is selected from the group consisting of TgyrA, Tsero_aroC, and TcodBA.

11. The DNA construct of claim 9, wherein each of the sequences in (iii) has a distinct termination sequence.

12. The DNA construct of claim 3, wherein the sequence of interest is an endogenous gene or a heterologous gene, wherein the endogenous gene has at least one mutation sequence selected from the group consisting of:
   a. a single nucleotide insertion;
   b. an insertion of two or more nucleotides;
   c. an insertion of a nucleic acid sequence encoding one or more proteins;
   d. a single nucleotide deletion;
   e. a deletion of two or more nucleotides;
   f. a deletion of one or more coding sequences;
   g. a substitution of a single nucleotide;
   h. a substitution of two or more nucleotides;
   i. two or more non-contiguous insertions, deletions, and/or substitutions; and
   j. any combination thereof.

13. The DNA construct of claim 4, wherein the sequence of interest is from a *Bacillus* species selected from the group consisting of *B. coagulans*, *B. ginsengihumi*, *B. shackletonii*, *B. aerius*, *B. aerophilus*, *B. stratosphericus*, *B. licheniformis*, *B. sonorensis*, *B. amyloliquefaciens*, *B. velezensis*, *B. atrophaeus*, *B. pumilus*, *B. safensis*, *B. altitudinis*, *B. vallismortis*, *B. subtilis*, *B. tequilensis*, *B. mojavensis*, *B. carboniphilus*, *B. oleronius*, *B. sporothermodurans*, *B. acidicola*, *B. aquimaris*, *B. vietnamensis*, *B. marisflavi*, *B. seohaeanensis*, *B. endophyticus*, and *B. humi*.

14. The DNA construct of claim 4, wherein each of the sequences in (iii) are consecutive.

15. The DNA construct of claim 4, wherein the amino acid sequences of the sequences in (iii) are identical.

16. A vector comprising the DNA construct of claim 2.

17. A DNA construct comprising a sequence of interest, a positive selectable marker, and two copies of the α-subunit of phenylalanyl-tRNA ligase (PheS) as counterselectable markers, wherein each of the counterselectable markers have been independently codon optimized for a *Bacillus* species and have a maximum continuous identity length of 500 base pairs when aligned with each other, and wherein each counterselectable marker is operably linked to at least one promoter.

18. The DNA construct of claim 17, wherein the *Bacillus* species is selected from the group consisting of *B. coagulans, B. ginsengihumi, B. shackletonii, B. aerius, B. aerophilus, B. stratosphericus, B. licheniformis, B. sonorensis, B. amyloliquefaciens, B. velezensis, B. atrophaeus, B. pumilus, B. safensis, B. altitudinis, B. vallismortis, B. subtilis, B. tequilensis, B. mojavensis, B. carboniphilus, B. oleronius, B. sporothermodurans, B. acidicola, B. aquimaris, B. vietnamensis, B. marisflavi, B. seohaeanensis, B. endophyticus,* and *B. humi*.

19. The DNA construct of claim 17, wherein the counterselectable markers further comprise A309G/T255S mutations.

20. The DNA construct of claim 17, wherein one counterselectable marker comprises SEQ ID NO: 1, or a sequence at least 90% identical thereto, and the other comprises SEQ ID NO: 2, or a sequence at least 75% identical thereto.

21. The DNA construct of claim 17, wherein the at least one promoter operably linked to each counterselectable marker is constitutive, inducible, differentially inducible, endogenous, heterologous, synthetic, a dual promoter, or a tandem promoter cluster.

22. The DNA construct of claim 17, wherein the at least one promoter is selected from the group consisting of PliaG, P43, PliaI, PrpsF, Pspac, and Pspank.

23. The DNA construct of claim 17, wherein each counterselectable marker has a distinct operably linked promoter.

24. The DNA construct of claim 17, wherein each of the counterselectable markers further comprises a termination sequence.

25. The DNA construct of claim 24, wherein the termination sequence is selected from the group consisting of TgyrA, Tsero_aroC, and TcodBA.

26. The DNA construct of claim 24, wherein each counterselectable marker has a distinct termination sequence.

27. The DNA construct of claim 17, wherein the sequence of interest is an endogenous gene or a heterologous gene, wherein the endogenous gene has at least one mutation sequence selected from the group consisting of:
 a. a single nucleotide insertion;
 b. an insertion of two or more nucleotides;
 c. an insertion of a nucleic acid sequence encoding one or more proteins;
 d. a single nucleotide deletion;
 e. a deletion of two or more nucleotides;
 f. a deletion of one or more coding sequences;
 g. a substitution of a single nucleotide;
 h. a substitution of two or more nucleotides;
 i. two or more non-contiguous insertions, deletions, and/or substitutions; and
 j. any combination thereof.

28. The DNA construct of claim 17, wherein the two copies of the α-subunit of phenylalanyl-tRNA ligase (PheS) are consecutive.

29. The DNA construct of claim 17, wherein the amino acid sequences of the two copies of the α-subunit of phenylalanyl-tRNA ligase (PheS) are identical.

30. A vector comprising the DNA construct of claim 17.

* * * * *

UNITED STATES PATENT AND TRADEMARK OFFICE
CERTIFICATE OF CORRECTION

PATENT NO. : 11,299,753 B2
APPLICATION NO. : 17/397540
DATED : April 12, 2022
INVENTOR(S) : Tara F. Mahoney et al.

It is certified that error appears in the above-identified patent and that said Letters Patent is hereby corrected as shown below:

In the Claims

Claim 7, Column 35, Line number 59, "PilaI" should be changed to --PliaI--.

Signed and Sealed this
Seventh Day of June, 2022

Katherine Kelly Vidal
*Director of the United States Patent and Trademark Office*